US005792928A

United States Patent [19]

Sanchis et al.

[11] Patent Number: 5,792,928

[45] Date of Patent: Aug. 11, 1998

[54] NUCLEOTIDE SEQUENCES CODING FOR POLYPEPTIDES ENDOWED WITH A LARVICIDAL ACTIVITY TOWARDS LEPIDOPTERA

[75] Inventors: Vincent Sanchis, Cambridge, United Kingdom; Didier Lereclus, Paris, France; Ghislaine Menou, Paris, France; Marguerite-Marie Lecadet, Paris, France; Daniel Martouret, Saint-Cyr L'Ecole, France; Raymond Dedonder, Chatenay Malabry, France

[73] Assignees: Institut Pasteur; Institut National de la Recherche Agronomique, both of Paris, France

[21] Appl. No.: 461,551

[22] Filed: Jun. 5, 1995

Related U.S. Application Data

[62] Division of Ser. No. 251,652, May 31, 1994, abandoned, which is a continuation of Ser. No. 94,382, Jul. 21, 1993, abandoned, which is a continuation of Ser. No. 458,754, filed as PCT/FR88/00292 Jun. 9, 1988, abandoned.

[30] Foreign Application Priority Data

| | | | |
|---|---|---|---|
| Jun. 10, 1987 | [EP] | European Pat. Off. | 87 08090 |
| May 6, 1988 | [FR] | France | 88 401121 |

[51] Int. Cl.$^6$ ..................... C12N 15/82; C12N 15/29; A01H 4/00; A01H 5/00

[52] U.S. Cl. ..................... 800/205; 435/69.1; 435/416; 514/2; 530/350; 536/23.71; 536/24.1

[58] Field of Search ..................... 514/2; 424/405; 530/350; 435/69.1, 419; 800/205; 536/23.71, 24.1

[56] References Cited

U.S. PATENT DOCUMENTS

| | | | |
|---|---|---|---|
| 5,126,133 | 6/1992 | Payne et al. | 424/93 L |
| 5,188,960 | 2/1993 | Payne et al. | 435/252.3 |
| 5,246,852 | 9/1993 | Payne et al. | 435/252.31 |
| 5,593,881 | 1/1997 | Thompson et al. . | |
| 5,596,071 | 1/1997 | Payne et al. . | |
| 5,602,032 | 2/1997 | Liu et al. . | |

FOREIGN PATENT DOCUMENTS

| | | |
|---|---|---|
| 0228838 | 7/1987 | European Pat. Off. . |
| 0405810 B1 | 3/1996 | European Pat. Off. . |
| WO95/02693 | 1/1995 | WIPO . |

OTHER PUBLICATIONS

Klier et al. Cloning and expression in *Escherichia coli* of the crystal protein gene from *Bacillus thuringiensis* strain aizawa 7-29 amd comparison of the structural organization of genes from different serotypes. Mol. Biol. of Mic. Diff, Ninth Conference, Sep. 1986.

Vaeck et al. Transgenic plants protected from insect attack. Nature, vol. 328, 2 Jul. 1987, pp. 33-37.

Gordon-Kamm et al. Transformation of maize cells and regeneration of fertile transgenic plants. The Plant Cell, vol. 2, 603-618, Jul. 1990.

Jaquet, et al., *Appl. Env. Mic.*, vol. 53, No. 3, Mar. 1987, pp. 500-504.

Honigman et al., *Gene*, vol. 42, 1986, pp. 69-77.

Klier et al., *Mol. Boil. of Mic. Diff*, Ninth Conference, Sep. 1986, pp. 217-224.

Wong et al. *J. Biol. Chem.*, vol. 258, No. 3, Feb. 10, 1983, pp. 1960-1967.

Wabiko et al., *DNA*, vol. 5, No. 4, 1986, pp. 305-314.

Suggs et al., *PNAS*, vol. 78, No. 11, Nov. 1981, pp. 6613-6617.

*Primary Examiner*—Douglas W. Robinson
*Assistant Examiner*—Thomas Haas
*Attorney, Agent, or Firm*—Finnegan, Henderson, Farabow, Garrett & Dunner, L.L.P.

[57] ABSTRACT

This invention relates to plant cells, plants, and seeds expressing a polypeptide having larvicidal activity. In particular, the invention relates to plant cells, plants, and seeds expressing the N-terminal region of a polypeptide toxic against the larvae of Lepidoptera of the Noctuidae family, and preferably against *S.littoralis*.

12 Claims, 5 Drawing Sheets

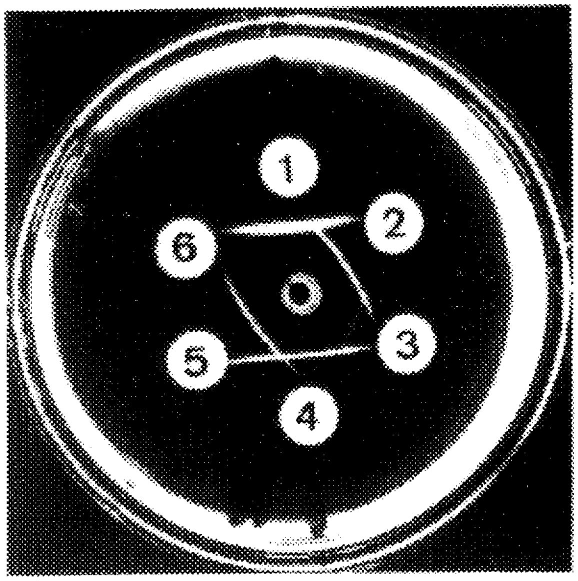
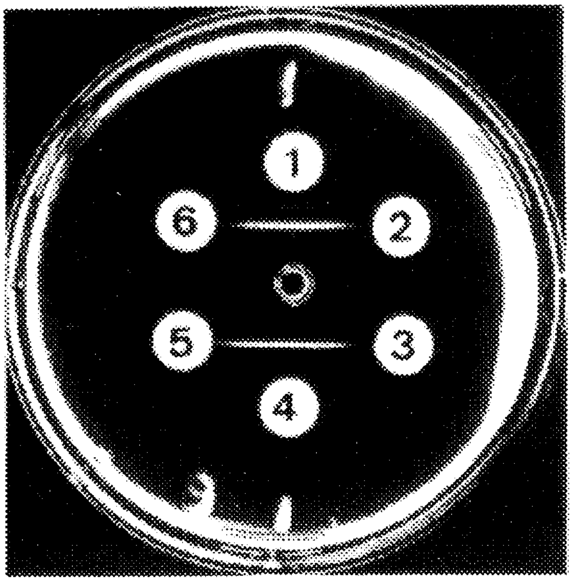
FIG. 5A
FIG. 5B

NUCLEOTIDE SEQUENCES CODING FOR POLYPEPTIDES ENDOWED WITH A LARVICIDAL ACTIVITY TOWARDS LEPIDOPTERA

This application is a divisional of application Ser. No. 08/251,652, filed May 31, 1994 (now abandoned), which is a continuation of Ser. No. 08/094,382, filed Jul. 21, 1993 (now abandoned), which is a continuation of Ser. No. 07/458,754, filed as PCT/FR88/00272 Jun. 9, 1988, (now abandoned).

BACKGROUND OF THE INVENTION

The subject of the invention is nucleotide sequences coding for polypeptides endowed with a larvicidal activity towards Lepidoptera.

It relates more particularly to agents, in particular nucleotide sequences, polypeptides or even vectors, or bacterial strains modified by these sequences and expressing polypeptides making it possible to prepare larvicidal compositions active against Lepidoptera, preferably against *Spodoptera littoralis* (hereafter *S.littoralis*) or *Mamestra brassicae* (hereafter designated by *M.brassicae*) or capable of transforming the plants to be treated in conferring on them this type of activity.

It is known that most of the isolates of *B.thuringiensis* show a toxic activity with regard to larvae of more than a hundred species of Lepidoptera.

This activity results from the capacity of the strains of *B.thuringiensis* to synthesize, at the moment of sporulation, crystalline inclusions of protein nature, or δ-endotoxins, under the control of one or several types of gene.

It has been shown that the activity of these polypeptides is contained in the $NH_2$-terminal half or N-terminus of the protein.

The studies carried out have shown the high specificity of the δ-endotoxins towards larvae of a given species.

On account of this high specificity, many species of Lepidoptera, in particular of the family of the Noctuidae, react only weakly to commercial preparations of available *B.thuringiensis*.

It is so in particular for the species *S.littoralis*, a polyphagous insect which constitutes the principal parasite of cotton and other industrially important crops. Among these crops, mention should be made of maiz, the castor oil plant, tobacco, the groundnut, fodder plants, such as clover or alfalfa, or also market garden produce such as the cabbage or the tomato.

Hence, one can imagine the interest of disposing of agents targeting specifically and effectively the family of the Noctuidae and in particular *S.littoralis* or *M.brassicae*.

The genes for δ-endotoxins hitherto identified do not code for a polypeptide preferentially active with regard to *S.littoralis*.

SUMMARY OF THE INVENTION

The search by the inventors for a sequence of nucleotides coding for a polypeptide preferably active against the Noctuidae, more especially against *S.littoralis*, has led them to study the natural isolates of two strains of *B.thuringiensis*, the larvicidal activity of which on *S.littoralis* appears to be higher than that of the industrial preparations made starting from other strains of *B.thuringiensis*.

The species in question are *aizawai* 7-29 and *entomodus* 6-01.

The study of these isolates has made it possible to demonstrate the existence of several genes for δ-endotoxins of different structures and different specificities, of which two genes preferentially active against *P.brassicae* but not very active against the Noctuida of cotton and a gene inactive against *P.brassicae* and *S.littoralis*.

By studying the total DNA of these isolates and by carrying out appropriate hybridizations, followed by the cloning of the fragments identified by hybridization, the inventors have observed that it is possible to isolate nucleotide sequences implicated in genes for δ-endotoxins coding for polypeptides active, preferably, against *S.littoralis*.

Thus, the aim of the invention is to provide nucleotide sequences capable of coding for at least the $NH_2$-terminal part of a δ-endotoxin toxic against the Noctuidae and preferably against *S.littoralis* or *M.brassicae*.

It also has the aim of providing a polypeptide toxic with regard to the Noctuidae.

Furthermore, the invention relates to a procedure for obtaining such a sequence and a polypeptide showing the desired activity as well as the intermediate agents such as vectors and bacterial strains which can be utilized for obtaining the polypeptide.

In addition, the invention relates to the uses of these sequences and polypeptides for the development of larvicidal compositions with regard to the Noctuidae, in particular *S.littoralis* and for the transformation of the plants likely to be infected by these larvae.

The invention relates to a sequence of nucleotides coding for at least a part of the N-terminal region of a polypeptide toxic specifically against the larvae of Lepidoptera of the Noctuidae family, and preferably against *S.littoralis*, characterized by its capacity of hybridization with a gene capable of expressing a polypeptide toxic towards larvae of *S.littoralis*.

According to another aspect of the invention, the nucleotide sequence is characterized in that it is carried by a sequence of nucleotides of about 3 kb such as obtained by in vitro genetic recombination of sequences of nucleotides of *B.thuringiensis* capable of hybridizing with probes 1, 2 and 3 of pHTA2 shown in FIG. 2. The fragment of 3 kb corresponds more particularly to the restriction fragment HindIII-PstI.

The sequences of nucleotides of the invention are, in addition, characterized in that they contain sites in the following order: HindIII-HincII-BglII-KpnI-HindIII-PstI.

In a preferred manner, these sequences of nucleotides are obtained by in vitro genetic recombination of DNA sequences derived from at least one strain of *B.thuringiensis*. In a variant of the embodiment of the invention, two different strains of *B.thuringiensis* are utilized.

Strains of *B.thuringiensis* particularly suited for obtaining these sequences of nucleotides are the strains corresponding to *aizawai* 7-29 and *entomodus* 6-01, deposited on 21 Apr., 1987 under the No. I-661 and No. I-660, respectively, with the National Collection of Cultures of Microorganisms (N.C.C.M.) in Paris.

In an advantageous manner, the sequences of nucleotides of the invention code for a polypeptide capable of forming an immunological complex with antibodies directed against polypeptides showing the larvicidal activity with regard to *S.littoralis*.

BRIEF DESCRIPTION OF THE DRAWINGS

FIG. 5 depicts the results of immunodiffusion tests.

DETAILED DESCRIPTION OF THE INVENTION

Figure 1:
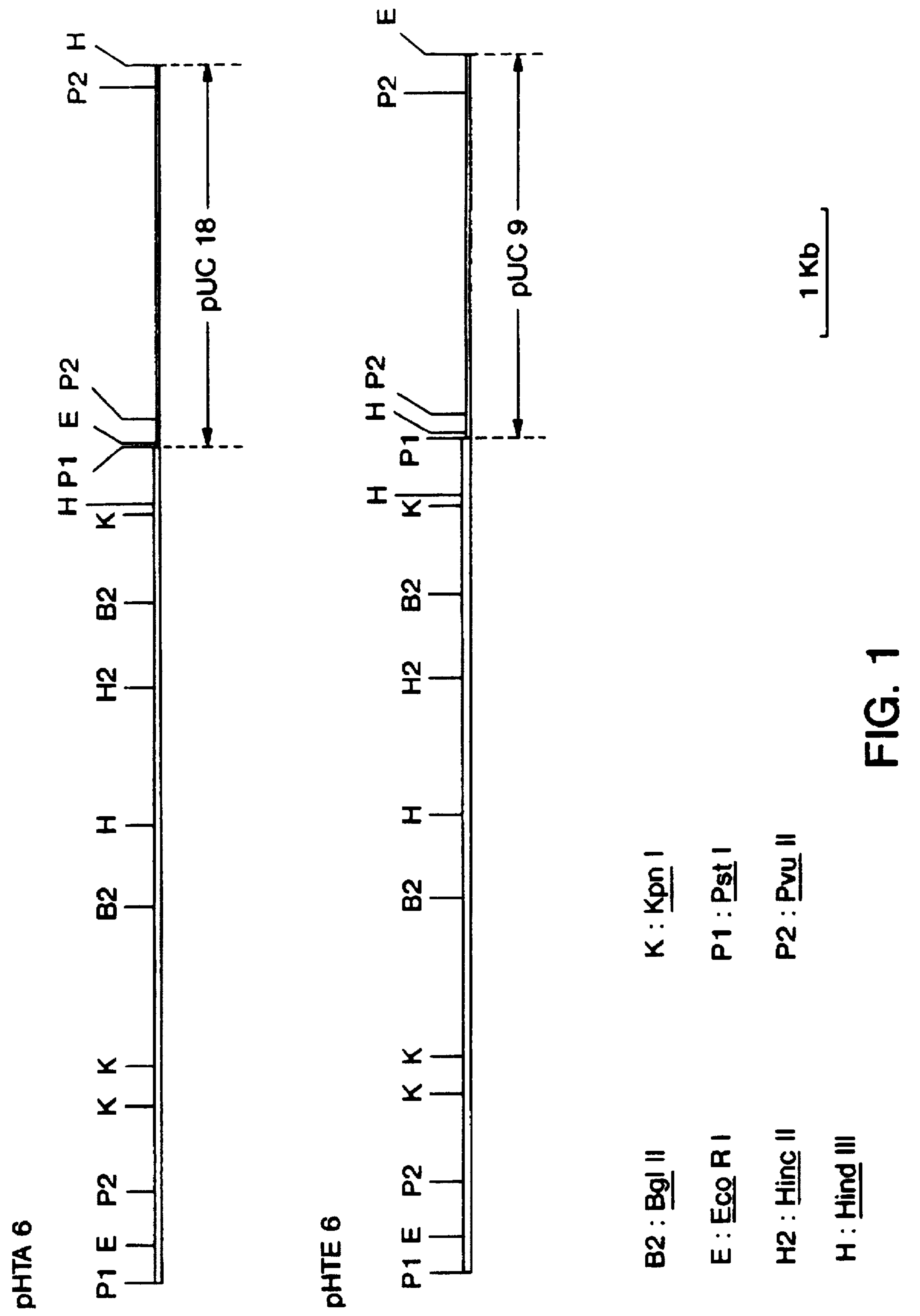
FIG. 1 depicts restriction maps of the plasmids pHTA6and pHTE6.

A sequence of nucleotides according to the invention is characterized in that it has the capacity to hybridize with a probe formed from the sequence (I) showing the following chain arrangement:

```
    52
GTC TAC TTG ACA GGG GTA GGA ACA TAA TCG GTC AAT TTT AAA
                            112
TAT GGG GCA TAT ATT GAT ATT TTA TAA AAT TTG TTA CGT TTT
                                                    172
TTG TAT TTT TTC ATA AGA TGT GTC ATA TGT ATT AAA TCG TGG

TAA TGA AAA ACA GTA TCA AAC TAT CAG AAC TTT GGT AGT TTA
                    232
ATA AAA AAA CGG AGG TAT TTT ATG GAG GAA AAT AAT CAA AAT
                                            292
CAA TGC ATA CCT TAC AAT TGT TTA AGT AAT CCT GAA GAA GTA

CTT TTG GAT GGA GAA CGG ATA TCA ACT GGT AAT TCA TCA ATT
            352
GAT ATT TCT CTG TCA CTT GTT CAG TTT CTG GTA TCT AAC TTT
                                    412
GTA CCA GGG GGA GGA TTT TTA GTT GCA TTA ATA GAT TTT GTA

TGG GGA ATA GTT GGC CCT TCT CAA TGG GAT GCA TTT CTA GTA
    472
CAA ATT GAA CAA TTA ATT AAT GAA AGA ATA GCT GAA TTT GCT
                            532
AGG AAT GCT GCT ATT GCT AAT TTA GAA GGA TTA GGA AAC AAT
                                                    592
TTC AAT ATA TAT GTG GAA GCA TTT AAA GAA TGG GAA GAA GAT

CCT AAT AAT CCA GAA ACC AGG ACC AGA GTA ATT GAT CGC TTT
                    652
CGT ATA CTT GAT GGG CTA CTT GAA AGG GAC ATT CCT TCG TTT
                                            712
CGA ATT TCT GGA TTT GAA GTA CCC CTT TTA TCC GTT TAT GCT

CAA GCG GCC AAT CTG CAT CTA GCT ATA TTA AGA GAT TCT GTA
            772
ATT TTT GGA GAA AGA TGG GGA TTG ACA ACG ATA AAT GTC AAT
                                    832
GAA AAC TAT AAT AGA CTA ATT AGG CAT ATT GAT GAA TAT GCT

GAT CAC TGT GCA AAT ACG TAT AAT CGG GGA TTA AAT AAT TTA
    892
CCG AAA TCT ACG TAT CAA GAT TGG ATA ACA TAT AAT CGA TTA
                            952
CGG AGA GAC TTA ACA TTG ACT GTA TTA GAT ATC GCC GCT TTC

TTT CCA AAC TAT GAC
```

Sequences of nucleotides coding for at least a part of the N-terminal region of a polypeptide toxic specifically towards larvae of Lepidoptera of the Noctuidae family, and preferably towards *S.littoralis*, are characterized in that they contain the chain arrangement (I) defined above.

In an advantageous manner, the sequence of nucleotides characterized by the chain arrangement defined above codes for a part of a polypeptide having a higher larvicidal activity towards *S.littoralis* than that of the polypeptides encoded by natural isolates presently known for their effects against *S.littoralis*.

The study of this sequence of nucleotides shows that it is characterized by an initiation codon ATG situated at position 241 starting from which an open reading frame of 750 nucleotides has been identified.

This sequence is also characterized by a GGAGG attachment site for ribosomes at positions 230 to 234.

According to another feature, the sequence of nucleotides of the invention is characterized in that it contains, upstream from the ATG codon, a sequence going from the nucleotide at position 137 to the nucleotide at position 177, strongly homologous with the region found by Wong et al. (1983) and described in (16) upstream from the gene for the crystal of the strain *kurstaki* HDl Dipel (BTK) and for which the authors have shown that it contains three promoters BtI, BtII and Ec which are functional in *B.thuringiensis* and *E.coli*, respectively. The homology of these sequences is about 70%.

The invention also relates to a sequence of nucleotides coding for the following sequence (II) of amino acids:

| | | | | | | | | | | | | | |
|---|---|---|---|---|---|---|---|---|---|---|---|---|---|
| | | | | | | | MET | GLU | GLU | ASN | ASN | GLN | ASN |
| GLN | CYS | ILE | PRO | TYR | ASN | CYS | LEU | SER | ASN | PRO | GLU | GLU | VAL |
| LEU | LEU | ASP | GLY | GLU | ARG | ILE | SER | THR | GLY | ASN | SER | SER | ILE |
| ASP | ILE | SER | LEU | SER | LEU | VAL | GLN | PHE | LEU | VAL | SER | ASN | PHE |
| VAL | PRO | GLY | GLY | PHE | LEU | VAL | GLY | LEU | ILE | ASP | PHE | VAL | TRP |
| GLY | ILE | VAL | GLY | PRO | SER | GLN | TRP | ASP | ALA | PHE | LEU | VAL | GLN |
| ILE | GLU | GLN | LEU | ILE | ASN | GLU | ARG | ILE | ALA | GLU | PHE | ALA | ARG |
| ASN | ALA | ALA | ILE | ALA | ASN | LEU | GLU | GLY | LEU | GLY | ASN | ASN | PHE |
| ASN | ILE | TYR | VAL | GLU | ALA | PHE | LYS | GLU | TRP | GLU | GLU | ASP | PRO |
| ASN | ASN | PRO | GLU | THR | ARG | THR | ARG | VAL | ILE | ASP | PRG | PHE | ARG |
| ILE | LEU | ASP | GLY | LEU | LEU | GLU | ARG | ASP | ILE | PRO | SER | PHE | ARG |
| ILE | SER | GLY | PHE | GLU | VAL | PRO | LEU | LEU | SER | VAL | TYR | ALA | GLN |
| ALA | ALA | ASN | LEU | HIS | LEU | ALA | ILE | LEU | ARG | ASP | SER | VAL | ILE |
| PHE | GLY | GLU | ARG | TRP | GLY | LEU | THR | THR | ILE | ASN | VAL | ASN | GLU |
| ASN | TYR | ASN | ARG | LEU | ILE | ARG | HIS | ILE | ASP | GLU | TYR | ALA | ASP |
| HIS | CYS | ALA | ASN | THR | TYR | ASN | ARG | GLY | LEU | ASN | ASN | LEU | PRO |
| LYS | SER | THR | TYR | GLN | ASP | TRP | ILE | THR | TYR | ASN | ARG | LEU | ARG |
| ARG | ASP | LEU | THR | LEU | THR | VAL | LEU | ASP | ILE | ALA | ALA | PHE | PHE |
| PRO | ASN | TYR | ASP | | | | | | | | | | |

A better identification of the sequence of nucleotides isolated from the above strains, deposited with the NCCM has made it possible to observe that the nucleotide situated at position 273 is guanine (G), the amino acid resulting from the GTA codon thus being valine.

Now, the reading of the nucleotide corresponding to this position 273 in the application FR.8708090 of 10 Jun. 1987 had led to reporting thymine (T) and leucine as amino acid resulting from the TTA codon.

Another sequence of nucleotides of the invention is characterized by its capacity of hybridization with a probe formed from the sequence (III) showing the following chain arrangement:

1
AAG CTT CAA TAG AAT CTC AAA TCT CGA TGA CTG CTT AGT CTT TTT AAT ACT GTC TAC TTG ACA GGG GTA GGA ACA TAA TCG GTC AAT TTT

91
AAA TAT GGG GCA TAT ATT GAT ATT TTA TAA AAT TTG TTA CGT TTT TTG TAT TTT TTC ATA AGA TGT GTC ATA TGT ATT AAA TCG TGG TAA

181
TGA AAA ACA GTA TCA AAC TAT CAG AAC TTT GGT AGT TTA ATA AAA AAA CGG AGG TAT TTT ATG GAG GAA AAT AAT CAA AAT CAA TGC ATA

271
CCT TAC AAT TGT TTA AGT AAT CCT GAA GAA GTA CTT TTG GAT GGA GAA CGG ATA TCA ACT GGT AAT TCG TCA ATT GAT ATT TCT CTG TCA

361
CTT GTT CAG TTT CTG GTA TCT AAC TTT GTA CCA GGG GGA GGA TTT TTA GTT GGA TTA ATA GAT TTT GTA TGG GGA ATA GTT GGC CCT TCA

451
CAA TGG GAT GCA TTT CTA GTA CAA ATT GAA CAA TTA ATT AAT GAA AGA ATA GCT GAA TTT GCT AGG AAT GCT GCT ATT GCT AAT TTA GAA

541
GGA TTA GGA AAC AAT TTC AAT ATA TAT GTG GAA GCA TTT AAA GAA TGG GAA GAA GAT CCT AAT AAT CCA GCA ACC AGG ACC AGA GTA ATT

631
GAT CGC TTT CGT ATA CTT GAT GGG CTA CTT GAA AGG GAC ATT CCT TCG TTT CGA ATT TCT GGA TTT GAA GTA CCC CTT TTA TCC GTT TAT

721
GCT CAA GCG GCC AAT CTG CAT CTA GCT ATA TTA AGA GAT TCT GTA ATT TTT GGA GAA AGA TGG GGA TTG ACA ACG ATA AAT GTC AAT GAA

811
AAC TAT AAT AGA CTA ATT AGG CAT ATT GAT GAA TAT GCT GAT CAC TGT GCA AAT ACG TAT AAT CGG GGA TTA AAT AAT TTA CCG AAA TCT

901
ACG TAT CAA GAT TGG ATA ACA TAT AAT CGA TTA CGG AGA GAC TTA ACA TTG ACT GTA TTA GAT ATC GCC GCT TTC TTT CCA AAC TAT GAC

991
AAT AGG AGA TAT CCA ATT CAG CCA GTT GGT CAA CTA ACA AGG GAA GTT TAT ACG GAC CCA TTA ATT AAT TTT AAT CCA CAG TTA CAG TCT

1081
GTA GCT CAA TTA CCT ACT TTT AAC GTT ATG GAG AGC AGC GCA ATT AGA AAT CCT CAT TTA TTT GAT ATA TTG AAT AAT CTT ACA ATC TTT

1171
ACG GAT TGG TTT AGT GTT GGA CGC AAT TTT TAT TGG GGA GGA CAT CGA GTA ATA TCT AGC CTT ATA GGA GGT GGT AAC ATA ACA TCT CCT

1261
ATA TAT GGA AGA GAG GCG AAC CAG GAG CCT CCA AGA TCC TTT ACT TTT AAT GGA CCG GTA TTT AGG ACT TTA TCA ATT CCT ACT TTA CGA

1351
TTA TTA CAG CAA CCT TGC CAG CGC CAC CAT TTT AAT TTA CGT GGT GGT GAA GGA GTA GAA TTT TCT ACA CCT ACA AAT AGC TTT ACG TAT

1441
CGA GGA AGA GGT ACG GTT GAT TCT TTA ACT GAA TTA CCG CCT GAG GAT AAT AGT GTG CCA CCT CGC GAA GGA TAT AGT CAT CGT TTA TGT

1531
CAT GCA ACT TTT GTT CAA AGA TCT GGA ACA CCT TTT TTA ACA ACT GGT GTA GTA TTT TCT TGG ACG CAT CGT AGT GCA ACT CTT ACA AAT

1621
ACA ATT GAT CCA GAG AGA ATT AAT CAA ATA CCT TTA GTG AAA GGA TTT AGA GTT TGG GGG GGC ACC TCT GTC ATT ACA GGA CCA GGA TTT

-continued

1711
ACA GGA GGG GAT ATC CTT CGA AGA AAT ACC TTT GGT GAT TTT GTA TCT CTA CAA GTC AAT ATT AAT TCA CCA ATT ACC CAA AGA TAC CGT

1801
TTA AGA TTT CGT TAC GCT TCC AGT AGG GAT GCA CGA GTT ATA GTA TTA ACA GGA GCG GCA TCC ACA GGA GTG GGA GGC CAA GTT AGT GTA

1891
GAT ATG CCT CTT CAG AAA ACT ATG GAA ATA GGG GAG AAC TTA ACA TCT AGA ACA TTT AGA TAT ACC GAT TTT AGT AAT CCT TTT TCA TTT

1981
AGA GCT AAT CCA GAT ATA ATT GGG ATA AGT GAA CAA CCT CTA TTT GGT GCA GGT TCT ATT AGT AGC GGT GAA CTT TAT ATA GAT AAA ATT

2071
GAG ATT ATT CTA GCA GAT GCA ACA TTT GAA GCA GAA TCT GAT TTA GAA AGA GCA CAA AAG GCG GTG AAT GCC CTG TTT ACT TCT TCC AAT

2161
CAA ATC GGG TTA AAA ACC GAT GTG ACG GAT TAT CAT ATT GAT CAA GTA TCC AAT TTA GTG GAT TGT TTA TCA GAT GAA TTT TGT CTG GAT

2251
GAA AAG CGA GAA TTG TCC GAG AAA GCT AAA CAT GCG AAG CGA CTC AGT GAT GAG CGG AAT TTA CTT CAA GAT CCA AAC TTC AGA GGG ATC

2341
AAT AGA CAA CCA GAC CGT GGC TGG AGA GGA AGT ACA GAT ATT ACC ATC CAA GGA GGA GAT GAC GTA TTC AAA GAG AAT TAC GTC ACA CTA

2431
CCG GGT ACC GTT GAT GAG TGC TAT CCA ACG TAT TTA TAT CAG AAA ATA GAT GAG TCG AAA TTA AAA GCT TAT ACC CGT TAT GAA TTA AGA

2521
GGG TAT ATC GAA GAT AGT CAA GAC TTA GAA ATC TAT TTG ATC GCG TAC AAT GCA AAA CAC GAA ATA GTA AAT GTG CCA GGC ACG GGT TCC

2611
TTA TGG CCG CTT TCA GCC CAA AGT CCA ATC GGA AAG TGT GGA GAA CCG AAT CGA TGC GCG CCA CAC CTT GAA TGG AAT CCT GAT CTA GAT

2701
TGT TCC TGC AG

In a distinctive manner, sequences of nucleotides of the invention coding for a polypeptide toxic specifically towards larvae of Lepidoptera of the Noctuidae family, and preferably toward *S.littoralis* comprise or are constituted by the chain arrangement (III) previously defined.

The chain arrangement (III), comprised in the sequence of nucleotides of the invention contains 2711 nucleotides. This fragment includes in particular the potential promoter of the gene of the δ-endotoxin active on *S.littoralis*.

Sequences of nucleotides modified in relation to the chain arrangements (I) or (III) described above naturally enter into the framework of the present invention to the extent to which these modifications do not generate appreciable variations of the toxicity of the polypeptide coded by the modified sequence towards *S.littoralis*.

These modifications may, for example, consist of deletions, substitutions, recombinations.

Thus, the sequences of nucleotides (I) and (III) contain at their position 611 a variable nucleotide corresponding to adenine (A) in the sequence (I) and to cytosine (C) in the sequence (III). These nucleotides enter into the composition of the respective codons GAA and GCA which code respectively for the amino acids glutamic acid (GLU) and alanine (ALA) in the respective sequences II and IV.

Similarly, any sequence of nucleotides which can hybridize with that of the chain arrangements (I) or (III) such as obtained by reverse enzymatic transformation of the corresponding RNA or even by chemical synthesis also enter into the framework of the definitions of the invention.

The sequence of nucleotides of formula (III) starts with a ATG initiation codon situated at position 241 and which represents the start of an open reading frame of 2470 nucleotides.

The invention also relates to a sequence of nucleotides characterized in that it codes for a polypeptide containing the sequence (IV) of amino acids below:

MET GLU GLU ASN ASN GLN ASN GLN CYS ILE

271
PRO TYR ASN CYS LEU SER ASN PRO GLU GLU VAL LEU LEU ASP GLY GLU ARG ILE SER THR GLY ASN SER SER ILE ASP ILE SER LEU SER

361
LEU VAL GLN PHE LEU VAL SER ASN PHE VAL PRO GLY GLY GLY PHE LEU VAL GLY LEU ILE ASP PHE VAL TRP GLY ILE VAL GLY PRO SER

451
GLN TRP ASP ALA PHE LEU VAL GLN ILE GLU GLN LEU ILE ASN GLU ARG ILE ALA GLU PHE ALA ARG ASN ALA ALA ILE ALA ASN LEU GLU

541
GLY LEU GLY ASN ASN PHE ASN ILE TYR VAL GLU ALA PHE LYS GLU TRP GLU GLU ASP PRO ASN ASN PRO ALA THR ARG THR ARG VAL ILE

631
ASP ARG PHE ARG ILE LEU ASP GLY LEU LEU GLU ARG ASP ILE PRO SER PHE ARG ILE SER GLY PHE GLU VAL PRO LEU LEU SER VAL TYR

721
ALA GLN ALA ALA ASN LEU HIS LEU ALA ILE LEU ARG ASP SER VAL ILE PHE GLY GLU ARG TRP GLY LEU THR THR ILE ASN VAL ASN GLU

811
ASN TYR ASN ARG LEU ILE ARG HIS ILE ASP GLU TYR ALA ASP HIS CYS ALA ASN THR TYR ASN ARG GLY LEU ASN ASN LEU PRO LYS SER

901
THR TYR GLN ASP TRP ILE THR TYR ASN ARG LEU ARG ARG ASP LEU THR LEU THR VAL LEU ASP ILE ALA ALA PHE PHE PRO ASN TYR ASP

991
ASN ARG ARG TYR PRO ILE GLN PRO VAL GLY GLN LEU THR ARG GLU VAL TYR THR ASP PRO LEU ILE ASN PHE ASN PHE ASN PRO GLN LEU GLN SER

1081
VAL ALA GLN LEU PRO THR PHE ASN VAL MET GLU SER SER ALA ILE ARG ASN PRO HIS LEU PHE ASP ILE LEU ASN LEU ASN ASN LEU THR ILE PHE

1171
THR ASP TRP PHE SER VAL GLY ARG ASN PHE TYR TRP GLY GLY HIS ARG VAL ILE SER SER LEU ILE GLY GLY GLY GLY GLY ASN ILE THR SER PRO

1261
ILE TYR GLY ARG GLU ALA ASN GLN GLU PRO PRO ARG SER PHE THR PHE ASN GLY PRO VAL PHE ARG THR LEU SER LEU SER ILE PRO THR LEU ARG

1351
LEU LEU GLN GLN PRO CYS GLN ARG HIS HIS PHE ASN LEU ARG GLY GLY GLU GLY VAL GLU PHE SER THR PRO THR PRO THR ASN SER PHE THR TYR

1441
ARG GLY ARG GLY THR VAL ASP SER LEU THR GLU LEU PRO PRO GLU ASP ASN SER VAL PRO PRO ARG GLU GLY TYR GLY TYR SER HIS ARG LEU CYS

1531
HIS ALA THR PHE VAL GLN ARG SER GLY THR PRO PHE LEU THR THR GLY VAL VAL PHE SER TRP THR HIS ARG SER ARG SER ALA THR LEU THR ASN

1621
THR ILE ASP PRO GLU ARG ILE ASN GLU ILE PRO LEU VAL LYS GLY PHE ARG VAL TRP GLY GLY THR SER VAL ILE VAL ILE THR GLY PRO GLY PHE

1711
THR GLY GLY ASP ILE LEU ARG ARG ASN THR PHE GLY ASP PHE VAL SER LEU GLN VAL ASN ILE ASN SER PRO ILE PRO ILE THR GLN ARG TYR ARG

-continued

1801
LEU ARG PHE ARG TYR ALA SER SER ARG ASP ALA ARG VAL ILE VAL LEU THR GLY ALA ALA SER THR GLY VAL GLY VAL GLY GLY GLN VAL SER VAL

1891
ASN MEI PRO LEU GLN LYS THR MEI GLU ILE GLY GLU ASN LEU THR SER ARG THR PHE ARG TYR THR ASP PHE SER ASN PRO PHE SER PHE

1981
ARG ALA ASN PRO ASP ILE ILE GLY ILE SER GLU GLN PRO LEU PHE GLY ALA GLY SER ILE SER SER GLY GLU LEU TYR ILE ASP LYS ILE

2071
GLU ILE ILE LEU ALA ASP ALA THR PHE GLU ALA GLU SER ASP LEU GLU ARG ALA GLN LYS ALA VAL ASN ALA LEU PHE THR SER SER ASN

2161
GLN ILE GLY LEU LYS THR ASP VAL THR ASP TYR HIS ILE ASP GLN VAL SER ASN LEU VAL ASP CYS LEU SER ASP GLU PHE CYS LEU ASP

2251
GLU LYS ARG GLU LEU SER GLU LYS VAL LYS HIS ALA LYS ARG LEU SER ASP GLU ARG ASN LEU LEU GLN ASP PRO ASN PHE ARG GLY ILE

2341
ASN ARG GLN PRO ASP ARG GLY TRP ARG GLY SER THR ASP ILE THR ILE GLN GLY GLY ASP ASP VAL PHE LYS GLU ASN TYR VAL THR LEU

2431
PRO GLY THR VAL ASP GLU CYS TYR PRO THR TYR LEU TYR GLN LYS ILE ASP GLU SER LYS LEU LYS ALA TYR THR ARG TYR GLU LEU ARG

2521
GLY TYR ILE GLU ASP SER GLN ASP LEU GLU ILE TYR LEU ILE ALA TYR ASN ALA LYS HIS GLU ILE VAL ASN VAL PRO GLY THR GLY SER

2611
LEU TRP PRO LEU SER ALA GLN SER PRO ILE GLY LYS CYS GLY GLU PRO ASN ARG CYS ALA PRO HIS LEU GLU TRP ASN PRO ASP LEU ASP

2701
CYS SER CYS

The invention also relates to recombinant expression and cloning vectors comprising more particularly at least one sequence of nucleotides such as that defined above, in particular at least a part of the sequence of about 3 kb.

A specific recombinant vector is, for example, a plasmid containing the HindIII-PstI fragment of the sequence of nucleotides of the invention, inserted in a vector pUC9. A first preferred vector is the plasmid pHT71, the construction of which is reported in the assemblies below, which comprises a HindIII-PstI DNA fragment according to the invention constituted uniquely of DNA derived from the strain *aizawai* 7-29.

Figure 4:
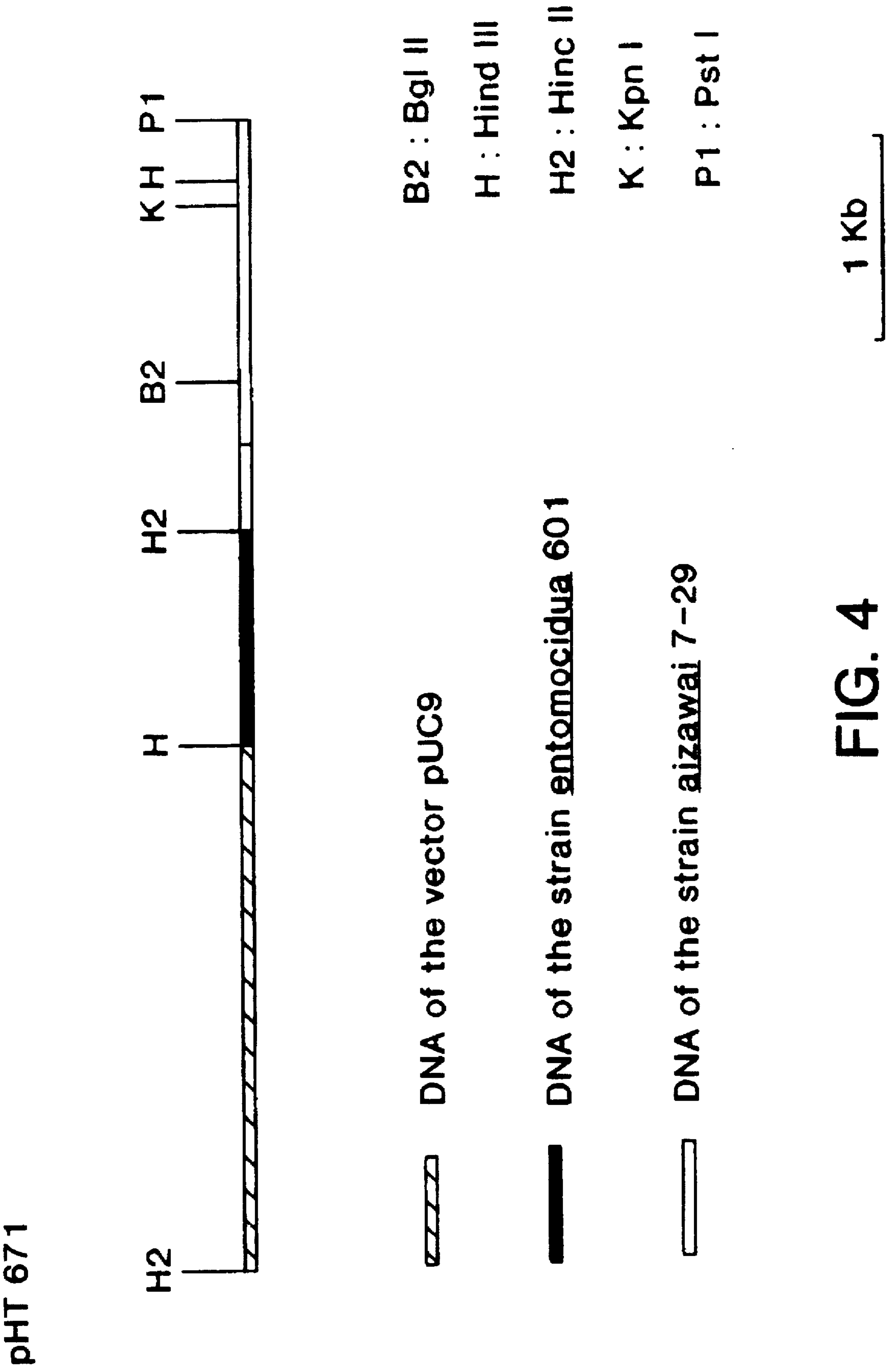
FIG. 4 depicts a restriction map of plasmid pHT 671 containing a chimeric HindIII-PstI fragment obtained by fusing a HindIII-HindII fragment of 1.1 kb derived from the strain *entomodus* 6-01 with a HincII-PstI fragment of 1.9 kb derived from the strain *aizawai* 7-29.

Another recombinant vector is constituted by the plasmid pHT 671, the construction of which is given in FIG. 4. This plasmid contains a chimeric HindIII-PstI fragment, obtained by fusing a HindIII-HindII fragment of 1.1 kb derived from the strain *entomocidus* 6-01 with a HincII-PstI fragment of 1.9 kb derived from the strain *aizawai* 7-29.

The modified bacterial strains which contain one of the nucleotide sequences defined above or also a recombinant expression vector and cloning previously defined, and preferably the plasmid pHT671 or the plasmid pHT71, also enter into the framework of the invention.

The invention also relates to a polypeptide toxic towards larvae of Lepidoptera and in a preferential manner towards *S.littoralis*, which attack cotton leaves or other crops such as those listed above, characterized in that it is capable of forming an immunological complex with antibodies directed against polypeptides with larvicidal activity towards *S.littoralis.*

The invention relates more particularly to the $NH_2$-terminal part of this polypeptide which contains the larvicidal activity.

The extremity of the active $NH_2$-terminal part corresponds to the sequence (II) of amino acids given above.

A preferred polypeptide of the invention is that which corresponds to this sequence (II) and corresponds to the sequence (IV) of amino acids given in the preceding pages. This polypeptide corresponding to the sequence (IV) contains 823 amino acids. Its calculated molecular mass is 92906 Da.

This sequence of δ-endotoxin was compared with amino acid sequences of δ-endotoxins derived from other strains of *B.thuringiensis* active on the Lepidoptera and the genes of which have been isolated and sequenced previously: the δ-endotoxins in question are those of the strains *kurstaki* HD1 (19), *kurstaki* HD73 (20), *berliner* 1715 (21) and (22) Sotto (23) and *aizawai* IPL7(24).

The results of these comparisons indicate that all are different in the second quarter of the molecule (amino acids 281 to 620) whereas the $NH_2$-terminal part (amino acids 1 to 280) and the COOH-terminal domain (amino acids 621 to 1175) of the protein are highly conserved and differ only by several amino acids. On the other hand, the δ-endotoxin corresponding to the sequence (IV) above shows considerable differences from the other δ-endotoxins both in the $NH_2$-terminal part (amino acids 1 to 280) and in the second quarter of the molecule (amino acids 281 to 620). The results of these comparisons indicate again that the $NH_2$-terminal half of the molecule (amino acids 1 to 620) which corresponds to the toxic fraction of the protein only show 46% homology with the other δ-endotoxins. The most important differences are located in the second half of the toxic part of the molecule (amino acids 281 to 620) with only 36% of identical amino acids, the $NH_2$-terminal part (amino acids 1 to 280) itself showing 58% of amino acids identical with the other δ-endo-toxins. Such considerable differences have never been observed up to now in the $NH_2$-terminal part of the toxic fraction of the molecule among the δ-endotoxins active on the Lepidoptera.

In order to obtain a sequence of nucleotides entering into the framework of the invention, coding for at least the active part of a polypeptide showing a specific toxicity towards larvae of Lepidoptera of the Noctuidae family, and preferably towards *S.littoralis*, recourse is had, in conformity with the invention, to the following steps, namely:

the carrying out of a molecular hybridization between, on the one hand, a nucleotide sequence of a strain of *B.thuringiensis* active against *S.littoralis* and, on the other, at least two nucleotide sequences, used as probes, derived from the 5' part of a restriction fragment of a gene for δ-endotoxin of *B.thurinpiensis*, this part coding for the $NH_2$-terminal part of the polypeptide active on the larvae of Lepidoptera, and from the 3' part of this fragment coding for the COOH part of the polypeptide, the isolation of the hybrid fragment, its cloning in a vector, followed by its purification.

In an advantageous manner, the hybridization probes utilized are obtained from a gene for the δ-endotoxin derived from the strain *aizawai* 7-29 coding for a protein of 130 kDa, active against *P.brassicae* and inactive towards *S.littoralis*, this gene having been cloned in the recombinant plasmid pHTA2.

In an embodiment of the preceding procedure, the fragment recombined with the vector in the cloning step is elaborated from a HindIII-PstI restriction fragment derived from a single strain of *B.thuringiensis*, preferably *aizawai* 7-29. In particular, this fragment is carried preferentially by the recombinant plasmid pHTA6 such as isolated with the aid of a probe constituted by a PvuII fragment of 2 kb of the plasmid pBT15-88 corresponding to the internal part of a gene for the chromosomal crystal of the strain *berliner* 1715, starting from transforming clones containing nucleotide sequences derived from *B.thuringiensis* strains active against larvae of Lepidoptera, inter-alia of *S.littoralis.*

In another embodiment of the invention, the fragment recombined with the vector in the cloning step is elaborated from several sequences of nucleotides derived from recombinant vectors containing sequences of nucleotides from at least two different strains of *B.thuringiensis*, possessing the same restriction maps and themselves containing all or part of the sequences of nucleotides capable of coding for a polypeptide active, in a preferential manner, against *S.littoralis.*

In this case, the recombined fragment used in the cloning step is a fragment of about 3 kb, advantageously elaborated from a HindIII-HincII restriction fragment of about 1.1 kb derived from the *entomocidus* 6-01 strain and a HincII-PstI fragment of about 1.9 kb from the *aizawai* 7-29 strain. It corresponds to a truncated gene for δ-endotoxin.

The HindIII-HincII and HincII-PstI restriction fragments are carried more especially by the respective recombinant plasmids pHTE6and pHTA6such as isolated with the aid of the probe constituted by the PvuII fragment mentioned above.

The study of the toxicity towards the larvae of Lepidoptera of the bacterial strains modified with the aid of the sequences of nucleotides defined above, has made it possible to demonstrate their high toxic activity, in particular with regard to the caterpillars of *S.littoralis.*

This activity was estimated from the point of view of the specificity index corresponding to the ratio $$\frac{LC50\ S.\ littoralis}{LC50\ P.\ brassicae}$$

in which "LC50 " represents the lethal concentration killing 50% of the larvae in 72 hours.

The utilization of such an index makes it possible to evaluate the activity of the bacterial strains studied without having to consider the level of expression of the polypeptides.

The results obtained, which are reported in the examples which follow, and the values of LD50 which are deduced from them, have shown that the bacterial strains modified according to the invention show a more specific toxic activity towards *S.littoralis* than the native crystal proteins of the strains *aizawai* 7-29 or *berliner* 1715.

Therefore, the invention relates to the use of these modified strains, of recombinant vectors containing the nucleotide sequences defined above, in particular the plasmid pHT671 and the plasmid pHT71, and these sequences themselves for the elaboration of larvicidal compositions preferentially toxic towards *S.littoralis.*

The larvicidal compositions of the invention are thus characterized in that they contain an efficaceous quantity of polypeptides such as defined above or expressed by the nucleotide sequences mentioned above.

In order to produce these polypeptides the truncated genes for δ-endotoxin corresponding to the nucleotide sequences of the invention are advantageously implemented.

These genes can be used to produce in excess the toxic polypeptide in microorganisms permitting the expression of the above recombinant vectors. Suitable strains of microorganisms include *E.coli* or also *B.subtilis.*

These truncated genes may be reintroduced into the strains of *B.thuringiensis* or into related species such as *B.cereus*, according to the standard techniques, for example, by transformation, conjugation or transduction. These techniques make it possible to produce the toxic polypeptide in large quantity without first having to modify the natural region of the promoter for the δ-endotoxin genes of *B.thuringiensis.*

This transformation may be carried out by using methods derived from the transformation of the protoplasts on *B.subtilis* according to (11) or of the vegetative cells of *B.thuringiensis* as described in (12).

The introduction of recombinant plasmids by a system of the conjugation type may be carried out by using *B.thuringiensis* as host strain and *B.subtilis* or *Streptococcus faecalis* as strains of the donor type by operating according to (13) and (14).

As a variant, the sequences of nucleotides are introduced into microorganisms living in the environment or in association with the plants and capable of expressing recombinant vectors containing these sequences. The introduction may be carried out in microorganisms such as Pseudomonas by working according to the procedure described in (17), by the intermediary of plasmid vectors containing the transposon $Tn_5$ and the gene for the toxin, or Azospirillum or Rhizobium by means of the intermediary of suicide vectors derived from the plasmid RP4and of mobilizing plasmids functional in Gram negative bacteria (for example, pRK2013) according to the procedures described in (18).

The truncated genes are alone in the strains of Bacilli or, as a variant, are associated with different δ-endotoxin genes which makes it possible to obtain crystals synthesized by these strains specifically toxic towards given species of Noctuidae, or toxic both towards the Noctuidae and insects sensitive to other δ-endotoxins. These recombinations, carried out in vitro or in vivo with the nucleotide sequences of the invention and other δ-endotoxin genes showing different toxic specificities, lead to the construction of new genes coding for novel hybrid toxic proteins exhibiting a large spectrum of activity towards insects. These new genes and these novel proteins also enter into the framework of the invention.

In these applications, the nucleotide sequences of the invention may be transferred and expressed in plants sensitive to *S.littoralis* in order to diminish the devastation caused by these insects.

Among the plants to be protected, mention should be made of: cotton, clover, the tomatoe and alfalfa.

The transfer of the truncated gene into cotton plants may be carried out by transformation involving strains such as Agrobacterium as described in (15).

In addition, the invention relates to the plant cells, the plants and the seeds containing the nucleotide sequences defined above.

The plant cells according to the invention are cells, the genome of which after transformation bv a non-essentially biological procedure possesses ina stable mannera sequence of nucleotides capable of expressing a polypeptide toxic towards *S.littoralis*, such as that defined above. The invention also relates to the plant cells derived from their division.

The plants according to the invention are plants transformed by a non-essentially biological procedure, having in particular as predator *S.littoralis*, the genome of which possesses in a stable manner a sequence of nucleotides such as that defined above, capable of expressing a polypeptide toxic towards *S.littoralis.* The plants in question are also plants derived from their reproduction, their multiplication or hybrid crosses.

In accordance with another feature, the invention relates to plants having in particular as predator *S.littoralis*, possessing in addition to their initial phenotypic and genotypic characters the property of expressing a polypeptide toxic preferentially towards *S.littoralis*, this property resulting from the insertion in their genome by means of genetic manipulation of a sequence of nucleotides capable of expressing the said polypeptide.

In addition, the invention relates to seeds capable of giving rise to a plant such as that defined above or derived from such a plant, characterized in that they have integrated into their genome by genetic manipulation a nucleotide sequence described above.

Figure 2:
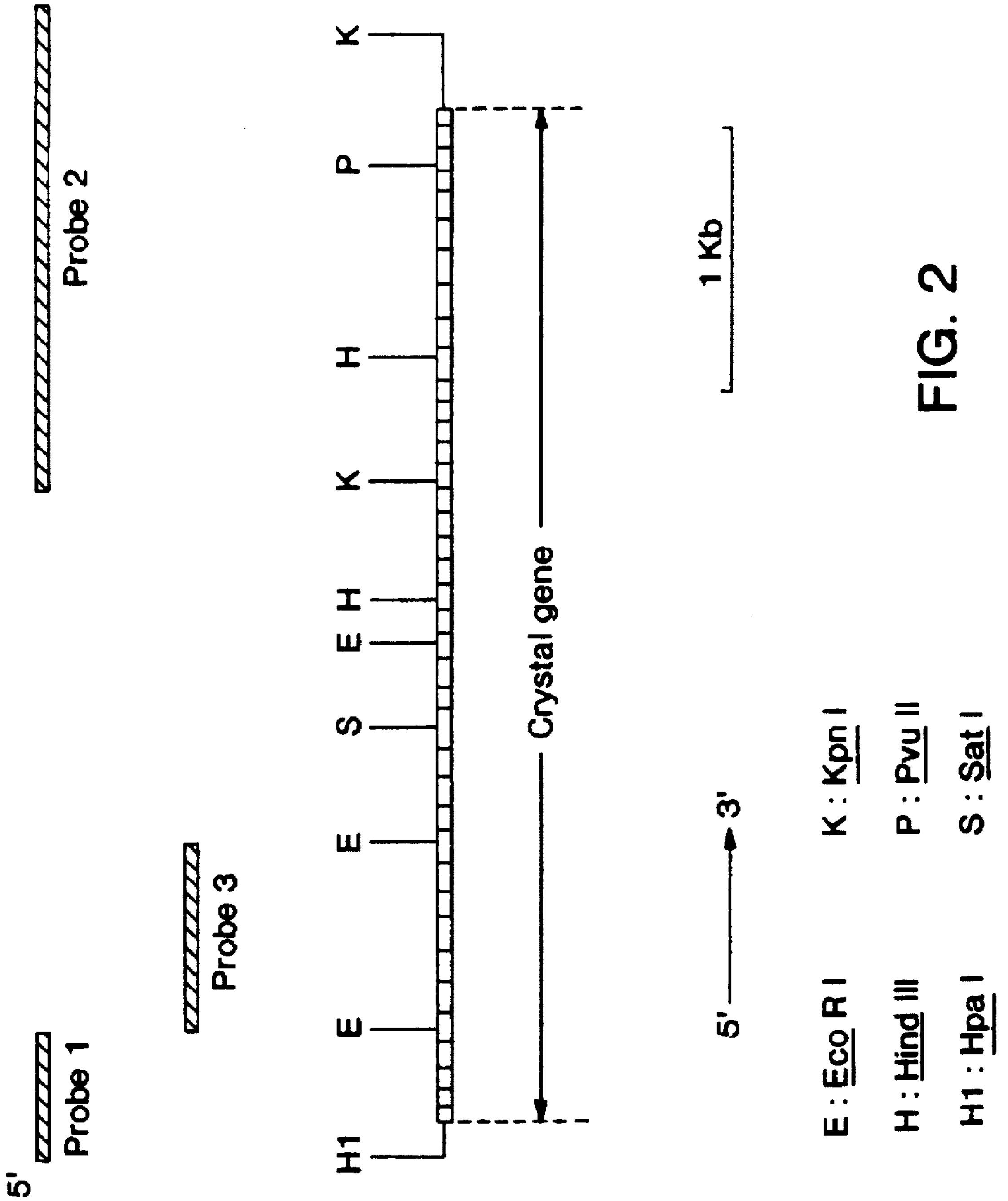
FIG. 2 depicts the restriction map of a gene for a crystal protein of the *aizawai* 7-29 strain cloned in the plasmid pHTA2and defines the DNA fragments that are used as probes 1, 2, and 3.
Figure 3:
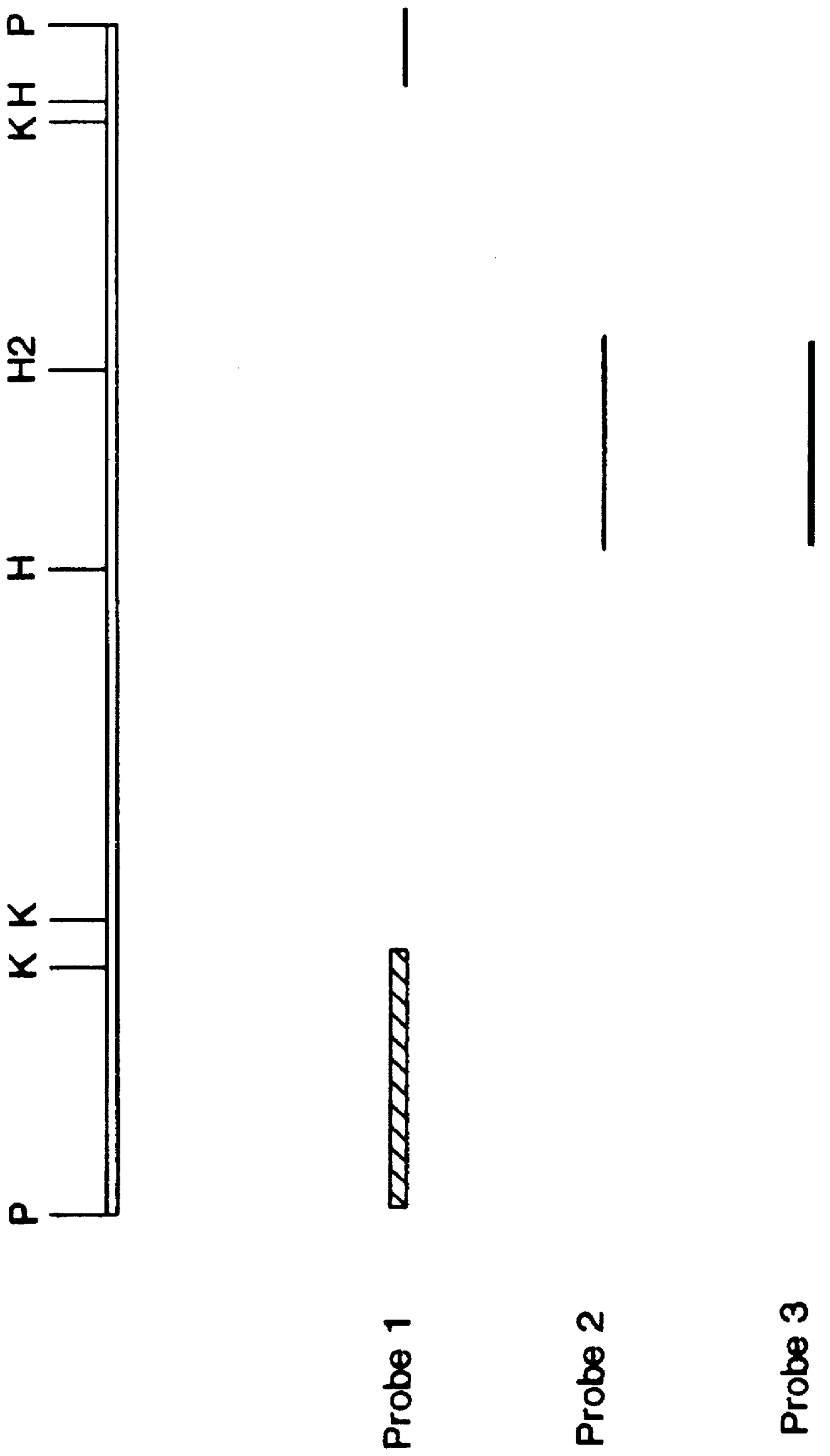
FIG. 3 depicts the fragment of 6.6 kb cloned in pHTA6and the result of hybridization experiments carried out between this fragment and probes 1, 2, and 3 described in FIG. 2.

Other characteristics and advantages of the invention will become apparent in the course of the description and in referring to the examples in which:

FIG. 1 presents the restriction map of the plasmids pHTA6 and pHTE6,

FIG. 2, the restriction map of a gene for a crystal protein of the *aizawai* 7-29 strain cloned in the plasmid pHTA2 and defining the DNA fragments which are used as probe, FIG. 3 shows the fragment of 6.6 kb cloned in pHTA6 and the result of a hybridization carried out between this fragment and the probes described in FIG. 2, FIG. 4, the restriction map of the plasmid pHT671, and FIG. 5, the photographs of the immunodiffusion tests.

The hybridization experiments carried out for the implementation of the invention were performed at 42° C. for 24 h in a solution containing 5× SSC, 30% formamide and 1 Denhardt (7) in the presence of the DNA probe labelled with $^{32}P$. The filters are washed at 42° C., 20 mn, by using successively the following solutions: 5× SSC in 30% formamide, 5× SSC, 2× SSC, 1× SSC and 0.5× C. SSC before drying at room temperature.

EXAMPLE 1

Construction of a DNA sequence of about 3 kb containing a hybrid gene of an insecticidal toxin.

This construction comprises:

1/ the preparation of gene banks of *B.thuringiensis*

2/ the selection and characterization of transforming clones containing the genes of a crystal protein and nucleotide sequences responsible for the larvicidal activity.

3/ in vitro recombination of these sequences in a cloning vector with construction of the plasmid pHT671.

These different steps are carried out as follows

1/ Preparation of gene banks of *B.thuringiensis.*

The total DNA of the *aizawai* 7-29 and *entomocidus* 7-01 strains of *Bacillus thuringiensis* is purified by using the method reported in (1) and 50 μg of each purified DNA are completely digested with the restriction enzyme PstI.

The DNA digested by PstI is analysed by horizontal electrophoresis on a 0.8% agarose gel and DNA fragments of a size of 5 to 8 kb are recovered from the agarose gels by electroelution in a manner described in (2).

The purified DNA fragments of 5–8 kb of the *aizawai* 7-29 strain are ligated to the DNA of the cloning vector pUC18 digested by PstI according to (3).

The purified DNA fragments of 5–8 kb of the *entomocidus* 6-01 chain are ligated to the DNA of the cloning vector pUC9digested by PstI. The cells of *E.coli* JD183 are transformed with the ligation mixture as described in (4).

The transforming clones of *E.coli* are selected on LB medium containing 100 μg/ml of ampicillin.

2/ Isolation and characterization of the transforming clones containing the genes for a crystal protein.

A/Screening of the transformed *E.coli* cells with the aid of an internal fragment of a gene of the crystal protein labelled with $^{32}$P, used as probe:

Transforming clones containing recombinant plasmids carrying the gene for the crystal are detected by colony hybridization according to the method described in (5), by using as probe a PvuII fragment of 2 kb of the pBT 15-88 plasmid corresponding to an internal part of the gene for the crystal protein located on the chromosome of the *berliner* 1715 strain.

B/ Characterization of the recombinant plasmids present in the clones which react with the above probe.

Two recombinant plasmids, pHTA6 and pHTE6, isolated respectively from gene banks constructed from the strains *aizawai* 7-29 and *entomocidus* 6-01, show a homology with this probe. In each case, a DNA fragment of about 6.6 kb was cloned.

The restriction map of the two plasmids is given in FIG. 1. The comparison of the restriction sites shows that the two DNA fragments cloned appear to be identical.

In order to delimit the sequences corresponding to the gene for the δ-endotoxin, different DNA fragments labelled with $^{32}$P, derived from a gene of the crystal previously characterized, and cloned in the recombinant plasmid pHTA2, are utilized as probes. This latter gene for the crystal also derived from the *aizawai* 7-29 strain codes for a protein of 130 kd active against *P.brassicae* but not against *S.littoralis.* This type of gene possesses the same restriction map as the gene for the δ-endotoxin derived from the *berliner* 1715 strain. In FIG. 2 is shown the restriction map of this gene for the crystal protein of the *aizawai* 7-29 strain cloned in the plasmid pHTA2. The thick lines shown above the map correspond to the fragments used as hybridization probes.

The plasmids pHTA6 and pHTE6 are hydrolysed by different restriction endonucleases, analysed by horizontal electrophoresis on a 0.8% agarose gel and hybridized with the different probes.

The transfer of the DNA to nitrocellulose filters is carried out according to the method of SOUTHERN described in (6). The hybridization is conducted at 42° C. for 24 hours in a solution containing: 5× SSC, 30% formamide and a 1× Denhardt mixture described in (7) in the presence of a DNA probe labelled with $^{32}$p. The filters are then washed at 42° C. for 20 minutes, by using successively the following solutions: 5 SSC in 50% formamide, 5 SSC, 2 SSC, 1 SSC and 0.5 SSC before being dried at room temperature.

The results of these hybridization experiments are summarized in FIG. 3. It appears that each extremity of the cloned DNA fragments of 6.6 kb shows a homology with the probes. The PstI-KpnI fragment of 1.5 kb reacting with the probe No. 3 corresponds to the 3' end of a gene of the crystal protein present in both the *aizawai* 7-29 and *entomocidus* 6-01 strains. As pointed out in FIG. 3, the probes No. 1 and No. 2 corresponding to the 5' end of the gene for the δ-endotoxin of pHTA2hybridize with the HindIII-HincI fragment of 1.1 kb contained in the plasmid pHTA6. The probe No. 3 which covers the 3' end of the gene of the δ-endotoxin of pHTA2 hybridizes with the HindIII-PstI fragment of 0.4 kb contained in the plasmid pHTA6. It should be noted that a weak hybridization signal is obtained with the probe No. 2 whereas the two other probes give easily detectable signals.

From these results, the inventors have established that the HindIII-PstI DNA fragment of 3 kb corresponds to a large part of a gene for the δ-endotoxin which commences close to the central HindIII site. It seems clear in the light of results of the hybridization experiments that the gene for the δ-endotoxin shows substantial differences from those characterized in the prior art. On the basis of these results it was decided to clone the HindIII-PstI fragment of 3 kb in the vector pUC9.

3/ Construction of the plasmid pHT 671 containing a hybrid gene of the reconstituted insecticidal toxin.

The HindIII-HincII DNA fragment of 1.1 kb derived from the plasmid pHTE6and the HincII-PstI DNA fragment of 1.9 kb derived from the plasmid pHTA6 are purified on agarose gels.

Equal amounts of the two purified DNA fragments and the DNA of pUC9 digested with HindIII and PstI are mixed and ligated. The ligation mixture is used to transform competent cells of *E.coli* JM83, then the transformed *E.coli* cells are selected on LB medium containing ampicillin. One of the interesting recombinant clones examined contains a plasmid designated by pHT671, the restriction map of which was determined and is shown in FIG. 4. This plasmid (pHT671) contains a DNA fragment of 3 kb inserted in the vector pUC9. This DNA sequence has the same restriction map as the HindIII-PstI fragments of 3 kb contained in the plasmids pHTA6and pHTE6, but corresponds to a reconstituted DNA molecule constructed by in vitro recombination from DNA sequences derived from the *aizawai* 7-29 strains on the one hand and *entomocidus* 6-01 on the other.

EXAMPLE II

Study of the nucleotide sequence of the promoter region and of the region coding for the $NH_2$-terminal part of the δ-endotoxin active against the Noctuidae.

The HindIII-HincII fragment of pHT671is sequenced in conformity with the method described in (8) by using a M13 system. In order to obtain partially overlapping cloned DNA fragments which will be used in the sequencing of the DNA, recourse is had to the method of subcloning by deletion in M13, developed by DALE et al (9).

The sequence of 940 nucleotides of the HindIII-HincII fragment which has a length of about 1 kilobase corresponds to the chain arrangement I above.

The analysis of this sequence shows that the largest open reading frame starts at position 241 and that a potential site of binding to the ribosomes, GGAGG, is found six base pairs upstream from this ATG codon (position 230 to 235). The region localized between the nucleotides 137 and 177 (position −103 to −63 upstream from the ATG codon) is strongly homologous with the region present upstream from the gene for the crystal of the strain *kurstaki* HD1Dipel (BTK) sequenced by WONG et al (1983) and described in (16) and the authors of which have shown that it contains three promoters BtI, BtII, and Ec, functional in *B.thuringiensis* and *E.coli*, respectively. The comparison between the amino acid sequences deduced from the first 750 nucleotides of the genes of BTK and pHT671, show that these polypeptides exhibit significant differences at the level of the N-terminal half of the active part derived from the protoxin (only 66% strict homology). It is important to note that it is the first time that a gene for the δ-endotoxin isolated from a strain active against the Lepidoptera codes for a polypeptide which shows substantial differences in this region. In fact, this N-terminal domain appears to be strongly conserved (more than 97% of strict homology) among all of the genes for the crystal active on Lepidoptera which have been sequenced hitherto. Moreover, the inventors have shown that the degree of variability is of the same order if the nucleotide sequences of pHT671and other genes of the Lepidoptera type are considered.

EXkMPLE III

Construction of a DNA sequence of about 2.7 kb containing a gene for a larvicidal toxin.

In order to achieve this construction the DNA of the *aizawai* 7-29 strain of *B.thuringiensis* was used up to the step for the production of the plasmid pHTA6as described in Example I.

The HindIII-PstI fragment of about 2.7 kb obtained from the plasmid pHTA6was then subcloned in the vector pUC9, previously hydrolysed by the restriction enzymes HindIII-PstI in order to give the plasmid pHT71.

EXAMPLE IV

Study of the sequence of nucleotides constituting the plasmid pHT71coding for a polypeptide toxic towards the larvae of Lepidoptera of the family of the Noctuidae.

The HindIII-PstI fragment of 2.7 kb of pHTA6, which was subcloned in pHT71, was sequenced by means of the technique of Sanger et al. (8) using the phage M13mp19 and the subcloning system by deletions developed by Dale et al (9). This system makes it possible to obtain M13 phages containing a series of partially overlapping DNA fragments which can be utilized for sequencing the DNA.

The sequence of nucleotides of this 2.7 kb fragment which corresponds to the chain arrangement (III) given above, was determined on the 2 DNA strands, with the exception of the last 212 nucleotides (position 2500 to 2711) which were sequenced only on a single strand.

The nucleotide sequence of this HindIII-PstI fragment has a length of 2711 nucleotides. This fragment contains the potential promoter as well as the largest part of the gene for the δ-endotoxin active on *S.littoralis*.

EXAMPLE V

Study of the specific toxicity of the recombinant clones of *E.coli* JM83(pHT671) and JM83 (pHT71) against *S.littoralis*.

The toxicity of the recombinant clones of *E.coli* JM83 containing pHT671and of *E.coli* JM83containing pHT71was determined by biological tests on caterpillars of the *P.brassicae* and *S.littoralis* species as described by LECADET and MARTOURET in (10). The results were compared with the specific toxicity of the native crystal proteins purified from the strains *berliner* 1715 and *aizawai* 7-29, *entomocidus* 7-01 *B.cereus* 569 (containing the plasmid pBT45, pAMB1 against the two species of insects. The specific toxicity of the recombinant clone and of the strains of *B.thuringiensis* is expressed in terms of "specificity index" previously defined.

The results obtained are reported in table 1 below.

In this table, for *E.coli* strains, the concentration 1 corresponds to a 14 hours bacterial culture concentrated 20 times, disintegrated by ultrasound ; for the *B.thuringiensis* strains the concentration is expressed in μg of crystal protein per μl of preparation. The toxic activity of the preparations was tested by the forced ingestion with 5 μl of preparation on caterpillars at the fifth stage of development, or by a technique of free ingestion utilizing larvae at the second stage of development.

TABLE 1

Comparative toxicity of a recombinant clone and two strains of *B. thuringiensis* towards *S. littoralis* and *P. brassicae.*

| | *S. littoralis P. brassicae* | | | Specificity index |
|---|---|---|---|---|
| Strains and plasmids | LC50 2nd larval stage | LC50 5th larval stage | LC50 5th larval stage | LC50 *S. littoralis* LC50 *P. brassicae* |
| JM83 (pUC18) | >1 | >1 | >1 | — |
| JM83 (pHT671) | 0.04 | 0.13 | 0.72 | 0.2 |
| JM83 (pHTA2) | >1 | >1 | 0.03 | >30 |
| JM83 (PHTA4) | >1 | >1 | >1 | — |
| JM83 (pHT71) | ND | 0.5 | >1 | >0.5 |
| *berliner* 1715 native crystals | ND | 0.11 | 0.007 | 15.7 |
| *aizawai* 7.29 native crystals | ND | 0.02 | 0.04 | 0.5 |
| *entomocidus* 601 native crystals | ND | 0.028 | 0.012 | 2.3 |
| *B. cereus* 569 (pBT45,pAMβ1) | ND | 0.38 | 0.054 | 7 |

Examination of the LC50 values summarized in this table 1 shows that the protein extracts of the recombinant clones JM83 (pHT671) and JM83 (pHT71) are preferentially toxic against *S.littoralis*. Secondly, a comparison of the values of the specificity index shows that the larvicidal activity of the recombinant clones is more specific by a facto of 2.5 times towards *S.littoralis* than the native crystal proteins of the *aizawai* strain. Moreover, the recombinant clones of J83 (pHT671) and JM83 (pHT71) are very active against another insect of the family of the Noctuidae, Mamestra brassicae (in the case of the clone JM83(pHT671) for example, the LC50 value is 0.02, utilizing larvae at the second stage of development).

These two results show that the gene for the larvicidal toxin constructed and cloned in the plasmids pHT671 and pHT71 codes for a protein specifically active against *S.littoralis*.

Other preparations obtained from recombinant clones containing plasmids carrying genes coding for other types of δ-endotoxins (pHTA2and pHTA4) are not active on *S.littoralis*: it may be seen that the plasmid pHTA2codes for a δ-endotoxin specifically active on *P.brassicae* whereas the plasmid pHTA4 codes for a δ-endotoxin, the insect target for which has not yet been identified. It can also be seen that the crystalline inclusions produced by a strain of Bacillus cereus which has received the plasmid pBT45, one of the plasmids of the *aizawai* 7-29 strain which also carries a δ-endotoxin gene (the gene of plasmid origin of the *aizawai* 7-29 strain), are also specifically active on *P.brassicae*.

Similar results are obtained by using, in the place of crude bacterial extracts, soluble protein extracts prepared from different recombinant clones of *E.coli*.

On the basis of the LC50 values reported in the table above and a mean individual weight of 41 mg per L5larva (fifth larval stage) of *S.littoralis*, the value of the LD50 was estimated at 2.4 μg/gram of larva for the native crystals of the *aizawai* 7-29 strain.

On these same bases and on the basis of equivalence factors making it possible to pass from the total bacterial mass to the quantity of specific proteins (about 2% of the total proteins in *E.coli* JM83 (pHT671), the LD50 corresponding to the toxin produced by the expression in *E.coli* JM83 of the gene according to the invention cloned in the plasmid pHT671, was determined and estimated at a value close to 5.5 to 6 μg/gram of larva.

On these same bases and after determination of the LC50 of soluble protein extracts prepared from ground cultures of *E.coli* JM83 (pHT671), the value of the LD50 corresponding to the toxin present in these extracts was estimated at 4.15 μg/gram of larva.

In the two cases and particularly in the case of the ground preparations of *E.coli*, the calculated values of LD50 are approximate and higher than that of the native crystals, because it is not a question of a purified toxin. However, these data indicate without ambiguity that the gene expressed by pHT671 specifies a δ-endotoxin exhibiting the specificity towards *S.littoralis*. In fact, the same type of estimation made with extract of *E.coli* JM83 (pHTA2) carrying a δ-endotoxin gene of different specificity leads to values 30 to 50 times higher than the LD50 of the soluble extracts towards *S.littoralis* (135 to 350 μg/gram of larva).

The foregoing data will easily make it possible for the person skilled in the art to develop active larvicidal compositions with the proteins of the invention.

Other toxicity experiments were carried out utilizing larvae of *M.brassicae*, *S.frugiperda* and *S.littoralis* at the second larval stage. The results obtained, expressed in terms of LC50 as defined for table 1, are given in table 2.

TABLE 2

ACTIVITY OF THE RECOMBINANT CLONES AGAINST THE LARVAE OF INSECTS OF THE FAMILY OF THE NOCTUIDAE: *M. BRASSICAE*, *S. FRUGIPERDA*, and *S. LITTORALIS*.

| STRAINS AND PLASMIDS | INSECT LARVAE AND STAGE: *M. BRASSICAE* LC50 2nd STAGE | *S. FRUGIPERDA* LC50 2nd STAGE | *S. LITTORALIS* LC50 2nd STAGE |
|---|---|---|---|
| JM 83 (pUC18) | NT | NT | NT |
| JM 83 (pHTA2) | >1 | 0,51 | 0,9 |
| JM 83 (pHT671) | 0,02 | 0,5 | 0,03 |
| JM 83 (pHT71) | ND | ND | 0,03 |
| JM 83 (pHTA4) | >1 | 0,54 | >1 |

It emerges from the examination of table 2 that the crude bacterial extracts of the recombinant clone JM83 (pHT671) are toxic towards *M.brassicae* and *S.littoralis* (the values of LC50 are 0.02 and 0.03, respectively) and weakly toxic towards *S.frugiperda* (LC50 of 0.5).

The extracts of the recombinant clone *E.coli* JM83 (pHTA2) are weakly active towards S.frugiperda and *S.littoralis* and not at all toxic towards *M.brassicae*. The extracts of the recombinant clone JI83 (pHTA4) are not toxic towards *M.brassicae* and *S.littoralis* and are weakly toxic toward *S.frugiperda*.

These results confirm the high specific toxicity of the proteins obtained from pHT71and pHT671 towards *S.littoralis* and show that this class of crystal protein is also very active towards *M.brassicae*.

EXAMPLE VI

Study of the specificity of the polypeptides expressed by the clones formed by introduction of the plasmids pHT671 and pHT71 into *E.coli*.

This study was carried out owing to immuno-diffusion tests. The results are reported in FIG. 5 (which includes FIGS. 5A and 5B).

The implementation of the immuno-diffusion experiment was done in conformity with the following protocol:

Soluble extracts of proteins of *E.coli* clones containing the plasmids pHT671, pHTA4, pHTA2or pHT71, pUC18were placed in the wells Nos. 2, 3, 4, 5, 6, respectively. A sample of a solubilized purified crystal of *aizawai* 7-29 was placed in the well No. 1 in order to serve as positive control.

In the test recorded in FIG. 5 A an antiserum against all of the δ-endotoxins of *aizawai* 7-29, containing rabbit antibodies directed against the solubilized crystal proteins, was used and placed in the central well.

An immunoprecipitation line was observed in all of the cases except in the case of the extract of *E.coli* containing only the plasmid vector (well No. 6).

It was observed that the immunoprecipitation lines derived from the wells No. 4 and No. 5 cross, which shows that the products encoded by the plasmids pHTA2and pHT71, respectively, display different antigenic determinants.

In the test recorded in FIG. 5B, the anti-serum used contained rabbit polyclonal antibodies against the crystal proteins of *berliner* 1715.

An immunoprecipitation line was observed with the extracts of *E.coli* JM83 (pHTA4) (well No. 3) JM83

(pHTA2) (well No. 4). On the other hand, the *E.coli* clones JM83 (pHT71) (well No. 5), JM83 (pHT671) (well No. 2) or JM83 (pUC9) (well No. 6) did not give immunoprecipitation.

It may be deduced from that that the genes for the crystal isolated in pHTA4 and pHTA2 express polypeptides having antigenic determinants in common with the proteins of the crystal of *berliner* 1715, a strain which is not specifically active towards *S.littoralis.*

On the other hand, the crude extracts of *E.coli* containing the plasmids pHT671 and pHT71 contain polypeptides having antigenic determinants in common with the crystal proteins of the *aizawai* 7-29 strain, which are not related immunogenically with the crystal proteins of the *berliner* 1715 strain.

These results confirm those given previously with respect to the specificity of the genes isolated in the plasmids pHT71 and pHT671.

Antigen-antibody precipitation assays have made it possible to determine the level of expression of the δ-endotoxin genes in different recombinant clones.

The results obtained have shown that the crystal protein represents between 7 and 10% of the total cellular proteins of *E.coli* JM83 (pHTA2), between 2 and 3% in *E.coli* JM83 (pHT671) and between 0.5 and 1% in *E.coli* JM83 (pHTA4) and *E.coli* JM83 (pHT71).

The literature references cited in the examples are the following (1) KLIER, A. F., LECADET, M-M. and DEDONDER, R., 1973, Sequential modifications of RNA polymerase during sporogenesis in *Bacillus thurinciensis*, Eur. J. Biochem., 36: 317–327.

(2) MANIATIS, T., FRITSCH, E. F., SAMBROOK, J., 1982, Molecular cloning: A laboratory manual. Cold Spring Harbor Laboratory Press, New York (3) VIEIRA, J. and MESSING, J., 1982, The pUC plasmids, and M13mp7 derived system for insertion mutagenesis and sequencing with synthetic universal primers, Gene, 19: 259–268.

(4) LEDERBERG, E. M. and COHEN, S. N., 1974, Transformation of *Salmonella thvphimurium* by plasmid deoxyribonucleic acid, J. Bacteriol., 119: 1072–104.

(5) GRUNSTEIN, M. and HOGNESS, D. S., 1975, Colony hybridization, a method for the isolation of cloned DNAs that contain a specific gene, Proc. Natl. Acad. Sci. U.S.A., 72: 3961–3965;

(6) SOUTHERN, E. M., 1975, Detection of specific sequence among DNA fragments separated by gel electrophoresis, J. Molec. Biol., 98, 503–517.

(7) DENHARDT, D. T. 1976, A membrane filter taking for the detection of complementary DNA. Biochem. Biophys. Res. Comm., 23: 641–646.

(8) SANGER, F., NICKLENS, S. and COULSON, A. R., 1977, DNA sequencing with chain terminating inhibitors. Proc. Natl. Acad. Sci. U.S.A., 74: 5463–5467.

(9) DALE et al. (1985) A rapid single-stranded cloning strategy for producing a sequential series of overlapping clones for use in DNA, Plasmid 1985, 13: 31–40

(10) LECADET, M. M. et MARTOURET D. 1987, Host specificity of the *Bacillus thuringiensis* δ-endotoxin toward Lepidopteran species: *Spodoptera littoralis* Bdv and *Pieris brassicae* L. J. of Invert. Pathol., 49 (No. 1) 37–48.

(11) CHANG et al., 1979, High frequency transformation of *Bacillus subtilis* protoplasts by plasmid DNA-Mol Gen Genet 168:111 115

(12) HEIERSON et al., 1987, Transformation of vegetative cells of *Bacillus thuringiensis* by plasmid DNA, Journal of Bacteriology, March 1987, p.1147–1152.

(13) KLIER et al., 1983, Mating between *Bacillus subtilis* and *Bacillus thuringiensis* and transfer of cloned crystal genes, Mol Gen Genet (1983) 191:257 262

(14) LERECLUS et al., 1983, Isolation of a DNA, sequence related to several plasmids from *Bacillus thurinqiensis* after a mating involving the *Streptococcus faecalis* plasmid pAM β1, Mol Gen Genet (1983) 191:307–313

(15) UMBECK et al., 1987, Genetically transformed cotton (*Gossypium hirsutum L.*) plants —Biotechnology vol.5 March 1987.

(16) WONG et al., 1983, transcriptional and translational start sites for the *Bacillus thuringiensis* crystal protein gene. J. of Biol. Chem., 258: 1960–1967.

(17) OBUKOWICZ M.et al (1986). $Tn^5$ mediated integration of the δ-endotoxin gene from *B. thuringiensis* into the chromosome of root colonizing Pseudomonas. J. Bacteriol., 168, 982–989.

(18) SIMON, R. et al, (1983). A broad host range mobilization system for in vivo genetic engineering: transposon mutagenesis in Gram-negative bacteria. Biotechnology, 1, pp. 784–791.

(19) Schnepf et al, (1985) The amino acid sequence of a crystal protein from *Bacillus thuringiensis* deduced from the DNA base sequence *J BIOL Chem* 260: 6264–6372.

(20) Adang et al.(1985) Characterized full-length and truncated plasmid clones of the crystal protein of *Bacillus thuringiensis* subsp. *kurstaki* HD-73and their toxicity to Manduca sexta. Gene 36 289–300.

(21) Wabiko et al.(1986) *Bacillus thuringiensis* entomocidal protoxin gene sequence and gene product analysis. DNA 5: 305–314.

(22) Hofte et al, (1986) Structural and functional analysis of a cloned δ-endotoxin gene of *Bacillus thuringiensis berliner* 1715. *Eur J Biochem* 161: 273–280.

(23)Shibano et al.(1986) Complete structure of an insecticidal crystal protein gene from *Bacillus thuringiensis.* In: *Bacillus molecular genetics and biotechnolovy applications.* J. Ganesan, A. T., Hoch, J. A.(eds). Academic Press 307–320.

(24) Oeda et al.(1987) Nucleotide sequence of the insecticidal protein gene of *Bacillus thuringiensis* strain *aizawai* IPL7 and its high-level expression in *Escherichia coli.* Gene 53: 113–119.

We claim:

1. A plant cell which expresses a polypeptide which has larvicidal activity against *S. littoralis* and which forms a specific immunological complex with an antibody directed against a polypeptide of the amino acid sequence (II) or (IV).

2. A cell according to claim 1 wherein the larvicidal polypeptide comprises the amino acid sequence (II) or (IV).

3. A cell according to claim 1 wherein the larvicidal polypeptide comprises the N-terminal region of a delta-endotoxin which is toxic towards *S. littoralis* larvae and which is encoded by a sequence comprising about a 3 kb sequence of nucleotides corresponding to a HindIII-PstI restriction fragment derived from *Bacillus thuringiensis* var. *aizawai* 7-29, or a fragment of the delta-endotoxin which is toxic towards *S. littoralis* larvae.

4. A cell according to claim 1 wherein a DNA sequence encoding the larvicidal polypeptide is integrated into the genome of the cell.

5. A plant which has cells expressing a polypeptide which has larvicidal activity against *S. littoralis* and which forms a specific immunological complex with an antibody directed against a polypeptide of the amino acid sequence (II) or (IV).

6. A plant according to claim 5 wherein the larvicidal polypeptide comprises the amino acid sequence (II) or (IV).

7. A plant according to claim 5 wherein the larvicidal polypeptide comprises the N-terminal region of a delta-endotoxin which is toxic towards *S. littoralis* larvae and which is encoded by a sequence comprising about a 3 kb sequence of nucleotides corresponding to a HindIII-PstI restriction fragment derived from *Bacillus thuringiensis* var. *aizawai* 7-29, or a fragment of the delta-endotoxin which is toxic towards *S. littoralis* larvae.

8. A plant according to claim 5 wherein a DNA sequence encoding the larvicidal polypeptide is integrated into the genome of cells of the plant.

9. Seed which has cells expressing a polypeptide which has larvicidal activity against *S. littoralis* and which forms a specific immunological complex with an antibody directed against a polypeptide or the amino acid sequence (II) of (IV).

10. Seed according to claim 9 wherein the larvicidal polypeptide comprises the amino acid sequence (II) or (IV).

11. Seed according to claim 9 wherein the larvicidal polypeptide comprises the N-terminal region of a delta-endotoxin which is toxic towards *S. littoralis* larvae and which is encoded by a sequence comprising about a 3 kb sequence of nucleotides corresponding to a HindIII-PstI restriction fragment derived from *Bacillus thuringiensis* var. *aizawai* 7-29, or a fragment of the delta-endotoxin which is toxic towards *S. littoralis* larvae.

12. Seed according to claim 9 wherein a DNA sequence encoding the larvicidal polypeptide is integrated into the genome or cells of the seed.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2711 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

AAGCTTCAAT AGAATCTCAA ATCTCGATGA CTGCTTAGTC TTTTTAATAC TGTCTACTTG 60

ACAGGGGTAG GAACATAATC GGTCAATTTT AAATATGGGG CATATATTGA TATTTTATAA 120

AATTTGTTAC GTTTTTTGTA TTTTTTCATA AGATGTGTCA TATGTATTAA ATCGTGGTAA 180

TGAAAAACAG TATCAAACTA TCAGAACTTT GGTAGTTTAA TAAAAAAACG GAGGTATTTT 240

ATGGAGGAAA ATAATCAAAA TCAATGCATA CCTTACAATT GTTTAAGTAA TCCTGAAGAA 300

GTACTTTTGG ATGGAGAACG GATATCAACT GGTAATTACT CAATTGATAT TTCTCTGTCA 360

CTTGTTCAGT TTCTGGTATC TAACTTTGTA CCAGGGGGAG GATTTTTAGT TGGATTAATA 420

GATTTTGTAT GGGGAATAGT TGGCCCTTCT CAATGGGATG CATTTCTAGT ACAAATTGAA 480

CAATTAATTA ATGAAAGAAT AGCTGAATTT GCTAGGAATG CTGCTATTGC TAATTTAGAA 540

GGATTAGGAA ACAATTTCAA TATATATGTG GAAGCATTTA AAGAATGGGA AGAAGATCCT 600

AATAATCCAG CAACCAGGAC CAGAGTAATT GATCGCTTTC GTATACTTGA TGGGCTACTT 660

GAAAGGGACA TTCCTTCGTT TCGAATTTCT GGATTTGAAG TACCCCTTTT ATCCGTTTAT 720

GCTCAAGCGG CCAATCTGCA TCTAGCTATA TTAAGAGATT CTGTAATTTT TGGAGAAAGA 780

TTGGGATTGA CAACGATAAA TGTCAATGAA AACTATAATA GACTAATTAG GCATATTGAT 840

GAATATGCTG ATCACTGTGC AAATACGTAT AATCGGGGAT TAAATAATTT ACCGAAATCT 900

ACGTATCAAG ATTGGATAAC ATATAATCGA TTACGGAGAG ACTTAACATT GACTGTATTA 960

GATATCGCCG CTTTCTTTCC AAACTATGAC AATAGGAGAT ATCCAATTCA GCCAGTTGGT 1020

CAACTAACAA GGGAAGTTTA TACGGACCCA TTAATTAATT TTAATCCACA GTTACAGTCT 1080

GTAGCTCAAT TACCTACTTT TAACGTTATG GAGAGCAGCG CAATTAGAAA TCCTCATTTA 1140

TTTGATATAT TGAATAATCT TACAATCTTT ACGGATTGGT TTAGTGTTGG ACGCAATTTT 1200

TATTGGGGAG GACATCGAGT AATATCTAGC CTTATAGGAG GTGGTAACAT AACATCTCCT 1260

ATATATGGAA GAGAGGCGAA CCAGGAGCCT CCAAGATCCT TTACTTTTAA TGGACCGGTA 1320

TTTAGGACTT TATCAATTCC TACTTTACGA TTATTACAGC AACCTTGCCA GCGCCACCAT 1380

TTTAATTTAC GTGGTGGTGA AGGAGTAGAA TTTTCTACAC CTACAAATAG CTTTACGTAT 1440

GCAGGAAGAG GTACGGTTGA TTCTTTAACT GAATTACCGC CTGAGGATAA TAGTGTGCCA 1500

CCTCGCGAAG GATATAGTCA TCGTTTATGT CATGCAACTT TTGTTCAAAG ATCTGGAACA 1560

CCTTTTTTAA CAACTGGTGT AGTATTTTCT TGGACGCATC GTAGTGCAAC TCTTACAAAT 1620

ACAATTGATC CAGAGAGAAT TAATCAAATA CCTTTAGTGA AAGGATTTAG AGTTTGGGGG 1680

GGCACCTCTG TCATTACAGG ACCAGGATTT ACAGGAGGGG ATATCCTTCG AAGAAATACC 1740

TTTGGTGATT TTGTATCTCT ACAAGTCAAT ATTAATTCAC CAATTACCCA AAGATACCGT 1800

TTAAGATTTC GTTACGCTTC CAGTAGGGAT GCAGCAGTTA TAGTATTAAC AGGAGCGGCA 1860

TCCACAGGAG TGGGAGGCCA AGTTAGTGTA GATATGCCTC TTCAGAAAAC TATGGAAATA 1920

GGGGAGAACT TAACATCTAG AACATTTAGA TATACCGATT TTAGTAATCC TTTTTCATTT 1980

AGAGCTAATC CAGATATAAT TGGGATAAGT GAACAACCTC TATTTGGTGC AGGTTCTATT 2040

AGTAGCGTTG AACTTTATAT AGATAAAATT GAAATTATTC TAGCAGATGC AACATTTGAA 2100

-continued

GCAGAATCTG ATTTAGAAAG AGCACAAAAG GCGGTGAATG CCCTGTTTAC TTCTTCCAAT 2160

CAAATCGGGT TAAAAACCGA TGTGACGGAT TATCATATTG ATCAAGTATC CAATTTAGTG 2220

GATTGTTTAT CAGATGAATT TTGTCTGGAT GAAAAGCGAG AATTGTCCGA GAAAGTCAAA 2280

CATGCGAAGC GACTCAGTGA TGAGCGGAAT TTACTTCAAG ATCCAAACTT CAGAGGGATC 2340

AATAGACAAC CAGACCGTGG CTGGAGAGGA AGTACAGATA TTACCATCCA AGGAGGAGAT 2400

GACGTATTCA AAGAGAATTA CGTCACACTA CCGGGTACCG TTGATGAGTG CTATCCAACG 2460

TATTTATATC AGAAAATAGA TGAGTCGAAA TTAAAAGCTT ATACCCGTTA TGAATTAAGA 2520

GGGTATATCG AAGATAGTCA AGACTTAGAA ATCTATTTGA TCGCGTACAA TGCAAAACAC 2580

GAAATAGTAA ATGTGCCAGG CACGGGTTCC TTATGGCCGC TTTCAGCCCA AAGTCCAATC 2640

GGAAAGTGTG GAGAACCGAA TCGATGCGCG CCACACCTTG AATGGAATCC TGATCTAGAT 2700

TGTTCCTGCA G 2711

( 2 ) INFORMATION FOR SEQ ID NO:2:

( i ) SEQUENCE CHARACTERISTICS:
( A ) LENGTH: 823 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:2:

Met Glu Glu Asn Asn Gln Asn Gln Cys Ile Pro Tyr Asn Cys Leu Ser
1 5 10 15

Asn Pro Glu Glu Val Leu Leu Asp Gly Glu Arg Ile Ser Thr Gly Asn
20 25 30

Ser Ser Ile Asp Ile Ser Leu Ser Leu Val Gln Phe Leu Val Ser Asn
35 40 45

Phe Val Pro Gly Gly Gly Phe Leu Val Gly Leu Ile Asp Phe Val Trp
50 55 60

Gly Ile Val Gly Pro Ser Gln Trp Asp Ala Phe Leu Val Gln Ile Glu
65 70 75 80

Gln Leu Ile Asn Glu Arg Ile Ala Glu Phe Ala Arg Asn Ala Ala Ile
85 90 95

Ala Asn Leu Glu Gly Leu Gly Asn Asn Phe Asn Ile Tyr Val Glu Ala
100 105 110

Phe Lys Glu Trp Glu Glu Asp Pro Asn Asn Pro Ala Thr Arg Thr Arg
115 120 125

Val Ile Asp Arg Phe Arg Ile Leu Asp Gly Leu Leu Glu Arg Asp Ile
130 135 140

Pro Ser Phe Arg Ile Ser Gly Phe Glu Val Pro Leu Leu Ser Val Tyr
145 150 155 160

Ala Gln Ala Ala Asn Leu His Leu Ala Ile Leu Arg Asp Ser Val Ile
165 170 175

Phe Gly Glu Arg Trp Gly Leu Thr Thr Ile Asn Val Asn Glu Asn Tyr
180 185 190

Asn Arg Leu Ile Arg His Ile Asp Glu Tyr Ala Asp His Cys Ala Asn
195 200 205

Thr Tyr Asn Arg Gly Leu Asn Asn Leu Pro Lys Ser Thr Tyr Gln Asp
210 215 220

Trp Ile Thr Tyr Asn Arg Leu Arg Arg Asp Leu Thr Leu Thr Val Leu
225 230 235 240

-continued

| | | | | | | | | | | | | | | | |
|---|---|---|---|---|---|---|---|---|---|---|---|---|---|---|---|
| Asp | Ile | Ala | Ala | Phe | Phe | Pro | Asn | Tyr | Asp | Asn | Arg | Arg | Tyr | Pro | Ile |
| | | | | 245 | | | | | 250 | | | | | 255 | |
| Gln | Pro | Val | Gly | Gln | Leu | Thr | Arg | Glu | Val | Tyr | Thr | Asp | Pro | Leu | Ile |
| | | | 260 | | | | | 265 | | | | | 270 | | |
| Asn | Phe | Asn | Pro | Gln | Leu | Gln | Ser | Val | Ala | Gln | Leu | Pro | Thr | Phe | Asn |
| | | 275 | | | | | 280 | | | | | 285 | | | |
| Val | Met | Glu | Ser | Ser | Ala | Ile | Arg | Asn | Pro | His | Leu | Phe | Asp | Ile | Leu |
| | 290 | | | | | 295 | | | | | 300 | | | | |
| Asn | Asn | Leu | Thr | Ile | Phe | Thr | Asp | Trp | Phe | Ser | Val | Gly | Arg | Asn | Phe |
| 305 | | | | | 310 | | | | | 315 | | | | | 320 |
| Tyr | Trp | Gly | Gly | His | Arg | Val | Ile | Ser | Ser | Leu | Ile | Gly | Gly | Gly | Asn |
| | | | | 325 | | | | | 330 | | | | | 335 | |
| Ile | Thr | Ser | Pro | Ile | Tyr | Gly | Arg | Glu | Ala | Asn | Gln | Glu | Pro | Pro | Arg |
| | | | 340 | | | | | 345 | | | | | 350 | | |
| Ser | Phe | Thr | Phe | Asn | Gly | Pro | Val | Phe | Arg | Thr | Leu | Ser | Ile | Pro | Thr |
| | | 355 | | | | | 360 | | | | | 365 | | | |
| Leu | Arg | Leu | Leu | Gln | Gln | Pro | Cys | Gln | Arg | His | His | Phe | Asn | Leu | Arg |
| | 370 | | | | | 375 | | | | | 380 | | | | |
| Gly | Gly | Glu | Gly | Val | Glu | Phe | Ser | Thr | Pro | Thr | Asn | Ser | Phe | Thr | Tyr |
| 385 | | | | | 390 | | | | | 395 | | | | | 400 |
| Arg | Gly | Arg | Gly | Thr | Val | Asp | Ser | Leu | Thr | Glu | Leu | Pro | Pro | Glu | Asp |
| | | | | 405 | | | | | 410 | | | | | 415 | |
| Asn | Ser | Val | Pro | Pro | Arg | Glu | Gly | Tyr | Ser | His | Arg | Leu | Cys | His | Ala |
| | | | 420 | | | | | 425 | | | | | 430 | | |
| Thr | Phe | Val | Gln | Arg | Ser | Gly | Thr | Pro | Phe | Leu | Thr | Thr | Gly | Val | Val |
| | | 435 | | | | | 440 | | | | | 445 | | | |
| Phe | Ser | Trp | Thr | His | Arg | Ser | Ala | Thr | Leu | Thr | Asn | Thr | Ile | Asp | Pro |
| | 450 | | | | | 455 | | | | | 460 | | | | |
| Glu | Arg | Ile | Asn | Gln | Ile | Pro | Leu | Val | Lys | Gly | Phe | Arg | Val | Trp | Gly |
| 465 | | | | | 470 | | | | | 475 | | | | | 480 |
| Gly | Thr | Ser | Val | Ile | Thr | Gly | Pro | Gly | Phe | Thr | Gly | Gly | Asp | Ile | Leu |
| | | | | 485 | | | | | 490 | | | | | 495 | |
| Arg | Arg | Asn | Thr | Phe | Gly | Asp | Phe | Val | Ser | Leu | Gln | Val | Asn | Ile | Asn |
| | | | 500 | | | | | 505 | | | | | 510 | | |
| Ser | Pro | Ile | Thr | Gln | Arg | Tyr | Arg | Leu | Arg | Phe | Arg | Tyr | Ala | Ser | Ser |
| | | 515 | | | | | 520 | | | | | 525 | | | |
| Arg | Asp | Ala | Arg | Val | Ile | Val | Leu | Thr | Gly | Ala | Ala | Ser | Thr | Gly | Val |
| | 530 | | | | | 535 | | | | | 540 | | | | |
| Gly | Gly | Gln | Val | Ser | Val | Asn | Met | Pro | Leu | Gln | Lys | Thr | Met | Glu | Ile |
| 545 | | | | | 550 | | | | | 555 | | | | | 560 |
| Gly | Glu | Asn | Leu | Thr | Ser | Arg | Thr | Phe | Arg | Tyr | Thr | Asp | Phe | Ser | Asn |
| | | | | 565 | | | | | 570 | | | | | 575 | |
| Pro | Phe | Ser | Phe | Arg | Ala | Asn | Pro | Asp | Ile | Ile | Gly | Ile | Ser | Glu | Gln |
| | | | 580 | | | | | 585 | | | | | 590 | | |
| Pro | Leu | Phe | Gly | Ala | Gly | Ser | Ile | Ser | Ser | Gly | Glu | Leu | Tyr | Ile | Asp |
| | | 595 | | | | | 600 | | | | | 605 | | | |
| Lys | Ile | Glu | Ile | Ile | Leu | Ala | Asp | Ala | Thr | Phe | Glu | Ala | Glu | Ser | Asp |
| | 610 | | | | | 615 | | | | | 620 | | | | |
| Leu | Glu | Arg | Ala | Gln | Lys | Ala | Val | Asn | Ala | Leu | Phe | Thr | Ser | Ser | Asn |
| 625 | | | | | 630 | | | | | 635 | | | | | 640 |
| Gln | Ile | Gly | Leu | Lys | Thr | Asp | Val | Thr | Asp | Tyr | His | Ile | Asp | Gln | Val |
| | | | | 645 | | | | | 650 | | | | | 655 | |
| Ser | Asn | Leu | Val | Asp | Cys | Leu | Ser | Asp | Glu | Phe | Cys | Leu | Asp | Glu | Lys |

-continued

| | | | | | | | | | | | | | | | |
|---|---|---|---|---|---|---|---|---|---|---|---|---|---|---|---|
| | | | 660 | | | | | 665 | | | | | 670 | | |
| Arg | Glu | Leu | Ser | Glu | Lys | Val | Lys | His | Ala | Lys | Arg | Leu | Ser | Asp | Glu |
| | | 675 | | | | | 680 | | | | | 685 | | | |
| Arg | Asn | Leu | Leu | Gln | Asp | Pro | Asn | Phe | Arg | Gly | Ile | Asn | Arg | Gln | Pro |
| | 690 | | | | | 695 | | | | | 700 | | | | |
| Asp | Arg | Gly | Trp | Arg | Gly | Ser | Thr | Asp | Ile | Thr | Ile | Gln | Gly | Gly | Asp |
| 705 | | | | | 710 | | | | | 715 | | | | | 720 |
| Asp | Val | Phe | Lys | Glu | Asn | Tyr | Val | Thr | Leu | Pro | Gly | Thr | Val | Asp | Glu |
| | | | | 725 | | | | | 730 | | | | | 735 | |
| Cys | Tyr | Pro | Thr | Tyr | Leu | Tyr | Gln | Lys | Ile | Asp | Glu | Ser | Lys | Leu | Lys |
| | | | 740 | | | | | 745 | | | | | 750 | | |
| Ala | Tyr | Thr | Arg | Tyr | Glu | Leu | Arg | Gly | Tyr | Ile | Glu | Asp | Ser | Gln | Asp |
| | | 755 | | | | | 760 | | | | | 765 | | | |
| Leu | Glu | Ile | Tyr | Leu | Ile | Ala | Tyr | Asn | Ala | Lys | His | Glu | Ile | Val | Asn |
| | 770 | | | | | 775 | | | | | 780 | | | | |
| Val | Pro | Gly | Thr | Gly | Ser | Leu | Trp | Pro | Leu | Ser | Ala | Gln | Ser | Pro | Ile |
| 785 | | | | | 790 | | | | | 795 | | | | | 800 |
| Gly | Lys | Cys | Gly | Glu | Pro | Asn | Arg | Cys | Ala | Pro | His | Leu | Glu | Trp | Asn |
| | | | | 805 | | | | | 810 | | | | | 815 | |
| Pro | Asp | Leu | Asp | Cys | Ser | Cys | | | | | | | | | |
| | | | 820 | | | | | | | | | | | | |